US012661346B2

(12) United States Patent
Zhou et al.

(10) Patent No.: US 12,661,346 B2
(45) Date of Patent: Jun. 23, 2026

(54) **ANTI-AGING METHOD COMPRISING APPLYING *JWA* GENE**

(71) Applicant: Simcere Pharmaceutical Co., Ltd., Nanjing (CN)

(72) Inventors: Jianwei Zhou, Nanjing (CN); Xiong Li, Nanjing (CN); Yifan Wen, Nanjing (CN); Yefei Huang, Nanjing (CN); Dongyin Chen, Nanjing (CN); Jingwen Liu, Nanjing (CN); Jin Xu, Nanjing (CN); Aiping Li, Nanjing (CN)

(73) Assignee: SIMCERE PHARMACEUTICAL CO., LTD., Nanjing (CN)

( * ) Notice: Subject to any disclaimer, the term of this patent is extended or adjusted under 35 U.S.C. 154(b) by 997 days.

(21) Appl. No.: 17/502,038

(22) Filed: Oct. 14, 2021

(65) Prior Publication Data

US 2022/0023278 A1 Jan. 27, 2022

Related U.S. Application Data

(63) Continuation-in-part of application No. PCT/CN2019/097393, filed on Jul. 24, 2019.

(30) Foreign Application Priority Data

Jun. 21, 2019 (CN) .......................... 201910540728.6

(51) Int. Cl.
| *A61K 31/4439* | (2006.01) |
| *A61P 3/08* | (2006.01) |
| *A61P 9/00* | (2006.01) |
| *C07D 413/14* | (2006.01) |
| *A61P 39/06* | (2006.01) |

(52) U.S. Cl.
CPC ............ *A61K 31/4439* (2013.01); *A61P 3/08* (2018.01); *A61P 9/00* (2018.01); *C07D 413/14* (2013.01); *A61P 39/06* (2018.01)

(58) Field of Classification Search
CPC ..... A61K 31/4439; A61K 45/00; A61P 39/06; A61P 9/00; A61P 3/00; A61P 19/00; A61P 25/00; A61P 25/28; A61P 9/10
See application file for complete search history.

(56) References Cited

FOREIGN PATENT DOCUMENTS

| CN | 1208733 A | 2/1999 |
| CN | 1951503 A | 4/2007 |
| CN | 103239710 A | 8/2013 |
| CN | 106632299 A | 5/2017 |
| CN | 110201173 A | 9/2019 |
| WO | 2014183491 A1 | 11/2014 |

OTHER PUBLICATIONS

"Medicated Feed." NOAH (National Office of Animal Health), https://www.noah.co.uk/topics/regulation/medicated-feed/. Published May 2016. Accessed Apr. 4, 2025. (Year: 2016).*
Lo Monte, Fabio, et al. "Identification of Glycogen Synthase Kinase-3 Inhibitors with a Selective Sting for Glycogen Synthase Kinase-3α." Journal of Medicinal Chemistry, vol. 55, No. 9, May 2012, pp. 4407-4424. DOI.org (Crossref), https://doi.org/10.1021/jm300309a. (Year: 2012).*
Yang Ye, Deficiency of JWA induces premature aging via activating NF-KB signaling in mice, Doctoral Dissertations of Nanjing Medical University, Mar. 15, 2018, pp. E059-4, vol. 2018, No. 03, Chinese Doctoral Dissertations Full text Database, China.
Yu Wu, DNA repair protein JWA involves in aging regulation in mice, Doctoral Dissertation of Nanjing Medical University, Jul. 2016, pp. 3-12, 87, 97, vol. 2016, No. 07, Chinese Doctoral Dissertation full text database, China.
Jin Xu et al., DNA Repair and Cellular Homeostasis Regulation Based On Toxic Pathways, China Academic Journal, Jul. 2017, p. 13, China Academic Journal Electronic Publishing House, China.
Rui Chen et al., Identification of JWA as a novel functional gene responsive to environmental oxidative stress induced by benzo[a]pyrene and hydrogen peroxide, Free Radical Biology and Medicine, Feb. 2007, pp. 1704-1714, vol. 2007, No. 42, Elsevier, Netherlands.
Lijuan Xu et al., Research progress of JWA gene, Laboratory Medicine and Clinic, Sep. 2015, vol. 12, No. 18, pp. 2795-2798, Chongqing Municipal Health Commission, China.
Nanping Wang et al., The mechanism of JWA gene involved in cellular oxidative stress, Chinese Journal of Industrial Hygiene and Occupational Diseases, Jun. 2003, pp. 212-215, vol. 21, No. 3, Chinese Medical Association, China.
Shu-Han Miao et al., Astrocytic JWA Expression is Essential to Dopaminergic Neuron Survival in the Pathogenesis of Parkinson's Disease, CNS Neuroscience & Therapeutics, Feb. 2014, pp. 212-215, vol. 20, No. 8, Wiley-Blackwell, United States.
Ting Zhu et al., Regulation of a novel cell differentiation-associated gene, JWA during oxidative damage in K562 and MCF-7 cells, Journal of Biomedical Science, Oct. 2004, pp. 219-227, vol. 12, No. 1, BioMed Central, United Kingdom.

* cited by examiner

*Primary Examiner* — Clinton A Brooks
*Assistant Examiner* — Kyle Nottingham
(74) *Attorney, Agent, or Firm* — MATTHIAS SCHOLL P.C.; Matthias Scholl

(57) ABSTRACT

The disclosure provides an anti-aging method. The method includes applying JWA gene to produce or screen anti-aging products, or products associated with treatment of aging-related diseases, or anti-oxidation products, or products for maintaining homeostasis, or products associated with diagnosis of aging or aging-related diseases, or agonists of the JWA gene.

4 Claims, 36 Drawing Sheets

Specification includes a Sequence Listing.

```
tgacttcctgtaactgagcactgaggctcagtgcatctctatttagcactcctcttactgtctcatatttaactagtgtt
tccactggattgcagaagttttgaaggcagagcaggattacattttttctcctctttaaaaaaaaaagaaaagaaaagaa
aaaaacccacagtgctttcacagagcctcaaaagaactcgaaatacttgctggcattgtactgaatattctcaaccttt
tcccctaccagatacatccacaacaataaagttggagcaaggtagagaaaagttagtagatgtttataatgaaagcat
agaaaacaaatcagattaaagcactattaatagcaaacaagaatcgtgggctatcctattgctaataacaataatagtaa
catataactgtgaacctttattatacactaagcatttcctatacattccttcacttagcctcgtctatatggcagatgtt
ccattatcccactttacacatgaagacaccgaggctgggagagattaagtagtttctccaaagtcacctgccagagag
aaggagctgcgactctaattttgctttctctgacttcacaccatccattttccagaatcaagaaaacatgagcactca
ggaatattttcacattttaaactttattcaaaaagcagcacataagatatatcttagcactaattccatgcaatcaccaa
attttcctaaacaacagtagtagtagtaatttcttagagtcgctgtaagctccttactgtcttctgaattaataaggaa
aattaaattatgttttctagactttgcattagtatatttcattactttccaagttttcaaaaattggtgatctgagtaga
gtgaattcaccttgtctaagccacttaggggcttagagactctgttatcttagaaatcttcaccttagaattctacctat
tacattatacaattaaacaaactacttttttttctcatgcattgtaccaatcagcccccttaactgaaaaaagatgacctt
ggaagcttagaagagaattgacaacgaatacttcttttgccaggtctttgggctgggatacaaaacatcacgttatctat
gaatatattgtggtccctcagtgaaagctgtcaccaaatattgcaataaaactaagaaaacttttgaagtggaatgcata
tttctgcccagaaaatgctggatgcagaacaactagttcactgcagacaactgtttgctttaaaatgtaagcaacatgcc
cagctcaggactgaagtggccagagtgcctactttatcagaatggcatagcagtccaacaatttagcctagagagaacag
aggtggagaacaagaagagagtgaaaaaacagaccagcccttctgttctacatgacttctttccgttttgccaat
ctgatttcacacatagtgactcatggtgaaacagagaaaacatgggaattgcattcagatgtgtagaggttagtaagact
tagttttcaaagcagctcattctccattaacactgtagtcgccttccatttcatttcacttagattggcatctgcacag
ctgccaaattttttctctaagtcagagaacacactcctaggtaaaccttcaaaaaaggtatttcgaaggaggcagcttct
ctgctgctagagaaggcattgccacctcccttcagacaggggatttccgctagttgctttctgtcatttcgtctctattc
tgcactcagtcccttgttctgtctggaggttcctgttttcctgtacccaaccaagagccaatgaagaagtaaagaggagc
aaacacgcccgcccactcccaatttcctttgctctgctgtctgccaaccgcaaagccgaccgagacggagccgctgtcaa
ctctccaactcagctcagctgatcggttgccgccgccgccgccagattctggagcgaagaacgcaaagctgagaac
```

FIG. 35

JAC-4 content (1g/kg)

JAC-4 content (2g/kg)

SEQUENCE LISTING

```
<160> NUMBER OF SEQ ID NOS: 2

<210> SEQ ID NO 1
<211> LENGTH: 2114
<212> TYPE: DNA
<213> ORGANISM: Artificial Sequence
<220> FEATURE:
<223> OTHER INFORMATION: Fully synthetic

<400> SEQUENCE: 1
gaattcggca cgagccgaga cggagccgct gtcaactctc caactcagct cagctgatcg          60
gttgccgccg ccgccgccgc cagattctgg aggcgaagaa cgcaaagctg agaacatgga         120
```

-continued

```
cgttaatatc gccccactcc gcgcctggga cgatttcttc ccgggttccg atcgctttgc      180
ccggccggac ttcagggaca tttccaaatg gaacaaccgc gtagtgagca acctgctcta      240
ttaccagacc aactacctgg tggtggctgc catgatgatt tccattgtgg ggtttctgag      300
tcccttcaac atgatcctgg gaggaatcgt ggtggtgctg gtgttcacag ggtttgtgtg      360
ggcagcccac aataaagacg tccttcgccg gatgaagaag cgctacccca cgacgttcgt      420
tatggtggtc atgttggcga gctatttcct tatctccatg tttggaggag tcatggtctt      480
tgtgtttggc attactttc ctttgctgtt gatgtttatc catgcatcgt tgagacttcg      540
gaacctcaag aacaaactgg agaataaaat ggaaggaata ggtttgaaga ggacaccgat      600
gggcattgtc ctggatgccc tagaacagca ggaagaaggc atcaacagac tcactgacta      660
tatcagcaaa gtgaaggaat aaacataact tacctgagct agggttgcag cagaaattga      720
gttgcagctt gcccttgtcc agacctatgt tctgcttgcg tttttgaaac aggaggtgca      780
cgtaccaccc aattatctat ggcagcatgc atgtataggc cgaactatta tcagctctga      840
tgtttcagag agaagacctc agaaaccgaa agaaaaccac caccctccta ttgtgtctga      900
agtttcacgt gtgtttatga aatctaatgg gaaatggatc acacgatttc tttaagggaa      960
ttaaaaaaaa taaaagaatt acggctttta cagcaacaat acgattatct tataggaaaa     1020
aaaaaaatca ttgtaaagta tcaagacaat acgagtaaat gaaaaggctg ttaaagtaga     1080
tgacatcatg tgttagcctg ttcctaaatc cctagaattg taatgtgtgg gatataaatt     1140
agtttttatt attctcttaa aaatcaaaga tgatctctat cactttgcca cctgtttgat     1200
gtgcagtgga aactggttaa gccagttgtt catacttcct ttacaaatat aaagatagct     1260
gtttaggata ttttgttaca tttttgtaaa tttttgaaat gctagtaatg tgttttcacc     1320
agcaagtatt tgttgcaaac ttaatgtcat tttccttaag atggttacag ctatgtaacc     1380
tgtattattc tggacggact tattaaaata caaacagaca aaaataaaa caaaacttga     1440 gttctattta ccttgcacat ttttttgttgt tacagtgaaa aaaatggtcc aagaaaatgt     1500
ttgccatttt tgcattgttt cgttttaac tggaacattt agaagaagg aaatgaatgt     1560 gcatttatt aattccttag gggcacaagg aggacaataa tagctgatct tttgaaattt     1620
gaaaaacgtc tttagatgac caagcaaaaa gactttaaaa aatggtaatg aaaatggaat     1680
gcagctactg cagctaataa aaaattttag atagcaattg ttacaaccat atgcctttat     1740
agctagacat tagaattatg atagcatgag tttatacatt ctattatttt tcctcccttt     1800
ctcatgtttt tataaatagg taataaaaaa tgttttgcct gccaattgaa tgatttcgta     1860
gctgaagtag aaacatttag gtttctgtag cattaaattg tgaagacaac tggagtggta     1920
cttactgaag aaactctctg tatgtcctag aataagaagc aatgatgtgc tgcttctgat     1980
ttttcttgca ttttaaattc tcagccaacc tacagccatg atctttagca cagtgatatc     2040
accatgactt cacagacatg gtctagaatc tgtaccctta cccacatatg aagaataaaa     2100
ttgattaaag gtta                                                       2114
```

<210> SEQ ID NO 2
<211> LENGTH: 188
<212> TYPE: PRT
<213> ORGANISM: Artificial Sequence
<220> FEATURE:
<223> OTHER INFORMATION: Fully synthetic -continued

```
<400> SEQUENCE: 2

Met Asp Val Asn Ile Ala Pro Leu Arg Ala Trp Asp Asp Phe Phe Pro
1               5                   10                  15

Gly Ser Asp Arg Phe Ala Arg Pro Asp Phe Arg Asp Ile Ser Lys Trp
            20                  25                  30

Asn Asn Arg Val Val Ser Asn Leu Leu Tyr Tyr Gln Thr Asn Tyr Leu
        35                  40                  45

Val Val Ala Ala Met Met Ile Ser Ile Val Gly Phe Leu Ser Pro Phe
    50                  55                  60

Asn Met Ile Leu Gly Gly Ile Val Val Val Leu Val Phe Thr Gly Phe
65                  70                  75                  80

Val Trp Ala Ala His Asn Lys Asp Val Leu Arg Arg Met Lys Lys Arg
            85                  90                  95

Tyr Pro Thr Thr Phe Val Met Val Val Met Leu Ala Ser Tyr Phe Leu
            100                 105                 110

Ile Ser Met Phe Gly Gly Val Met Val Phe Val Phe Gly Ile Thr Phe
            115                 120                 125

Pro Leu Leu Leu Met Phe Ile His Ala Ser Leu Arg Leu Arg Asn Leu
    130                 135                 140

Lys Asn Lys Leu Glu Asn Lys Met Glu Gly Ile Gly Leu Lys Arg Thr
145                 150                 155                 160

Pro Met Gly Ile Val Leu Asp Ala Leu Glu Gln Gln Glu Glu Gly Ile
            165                 170                 175

Asn Arg Leu Thr Asp Tyr Ile Ser Lys Val Lys Glu
            180                 185
```

ANTI-AGING METHOD COMPRISING APPLYING *JWA* GENE

CROSS-REFERENCE TO RELATED APPLICATIONS

This application is a continuation-in-part of International Patent Application No. PCT/CN2019/097393 with an international filing date of Jul. 24, 2019, designating the United States, now pending, and further claims foreign priority benefits to Chinese Patent Application No. 201910540728.6 filed on Jun. 21, 2019. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to a JWA gene associated with anti-aging, and compounds capable of activating JWA gene expression and uses thereof JWA gene, also known as ARL6IP5 (GenBank Accession No. AF070523, 1998), is a stress-response gene that is discovered and cloned from a retinoic acid-induced differentiation model of human bronchial epithelial cells. JWA gene encodes a cytoskeleton binding protein, has active biological functions, and is ubiquitously and moderately expressed in normal tissues and cells. When physical and chemical factors of the environment act on the cells, JWA gene responds quickly, expresses sharply and plays the role of inhibiting oxidative stress and repairing DNA damage.

The inventors of this patent found in the preliminary research work that JWA gene is a novel tumor suppressor gene that controls a plurality of downstream regulating factors to inhibit tumor angiogenesis and metastasis and promote apoptosis. JWA polypeptide (PJP1) is screened and obtained and further used to synthesize a specific polypeptide targeting the integrins (PJP1-RGD). The specific polypeptide causes negligible toxic effects to cells and animals but can significantly inhibit the growth of melanoma tumor and gastric cancer cells, etc. in tumor-bearing mice.

SUMMARY

The disclosure provides a use of JWA gene as a target of anti-aging drugs. Specifically, JWA gene can be activated by the anti-aging drugs and expressed in the human body to exhibit anti-aging properties.

The disclosure provides an anti-aging method, the method comprises applying JWA gene (GenBank Accession No. AF070523) to produce or screen anti-aging products, or products associated with treatment of aging-related diseases, or anti-oxidation products, or products for maintaining homeostasis, or products associated with diagnosis of aging or aging-related diseases, or agonists of the JWA gene.

The disclosure also provides anti-aging method, the method comprising applying a JWA protein to produce or screen anti-aging products, or products associated with treatment of aging-related diseases, or anti-oxidation products, or products for maintaining homeostasis, or anti-aging methods, or methods associated with treatment of aging-related diseases, or anti-oxidation methods, or methods for maintaining homeostasis, or products associated with diagnosis of aging or aging-related diseases, or proteolytic enzyme inhibitors of the JWA protein; the JWA protein is coded by the JWA gene and has an amino acid sequence represented by SEQ ID NO: 2.

The aforesaid JWA gene is a full-length gene or a gene fragment of JWA gene; the JWA protein is a full-length protein or a protein fragment of JWA protein. The method further comprises activating the transcription of the JWA gene and/or inhibiting the enzymes intended to degrade the JWA protein.

The disclosure provides an anti-aging method, the method comprises applying a compound of formula (I) to produce anti-aging products, or products associated with treatment of aging-related diseases, or anti-oxidation products, or products for maintaining homeostasis:

In a class of this embodiment, the compound is in the form of the compound or a pharmaceutically acceptable salt thereof. The pharmaceutically acceptable salt is prepared by the reaction of the compound with hydrochloric acid, sulfuric acid, benzenesulfonic acid, p-toluenesulfonic acid, phosphoric acid, hydrobromic acid, maleic acid, fumaric acid or malic acid.

In a class of this embodiment, the compound is an isomer or a homologue of formula I.

In a class of this embodiment, the product includes but is not limited to preparations, probes, reagents, kits, healthcare products, medicines or pharmaceutical compositions.

In a class of this embodiment, the anti-aging comprises delaying aging, prolonging life, improving the appearance of aging-related changes. The maintaining homeostasis comprises maintenance of redox homeostasis, glucose and lipid homeostasis, and endocrine homeostasis.

In a class of this embodiment, the aging-related diseases comprise cardiovascular diseases, neurodegenerative diseases, bone diseases, and chronic metabolic diseases. The cardiovascular diseases comprise hypertension and atherosclerosis. The neurodegenerative diseases comprise Parkinson's disease and Alzheimer's disease. The bone diseases comprise osteoporosis and bone deformities. The chronic metabolic diseases comprise type 2 diabetes and alcoholic fatty liver diseases.

In a class of this embodiment, the anti-oxidation comprises an increase in reserves of antioxidant factors and removal of oxidative substances from the body. The antioxidant factors in the body comprise superoxide dismutase (SOD), catalase (CAT), and glutathione peroxidase (GSH-px). The oxidative substances in the body comprise reactive oxygen species (ROS), superoxide anions $O^{2-}$, hydrogen peroxide $H_2O_2$, and hydroxyl radicals $OH^-$.

In practical research conducted by the inventors, it is found that JWA gene is closely related with aging and therefore can be qualified as a target gene during anti-aging, for treatment of aging-related diseases, anti-oxidation, and maintenance of homeostasis.

Till the disclosure, there have been no small molecule compounds reported that can activate the expression of JWA gene in vivo to provide anti-aging effects. Therefore, the development of anti-aging drugs based on the JWA gene as a molecular target has bright application prospect.

BRIEF DESCRIPTION OF THE DRAWINGS

FIG. 35 shows a sequence of 2012 bp upstream of transcriptional start point of JWA gene in accordance with Example 8 of the disclosure;

Figure 48:
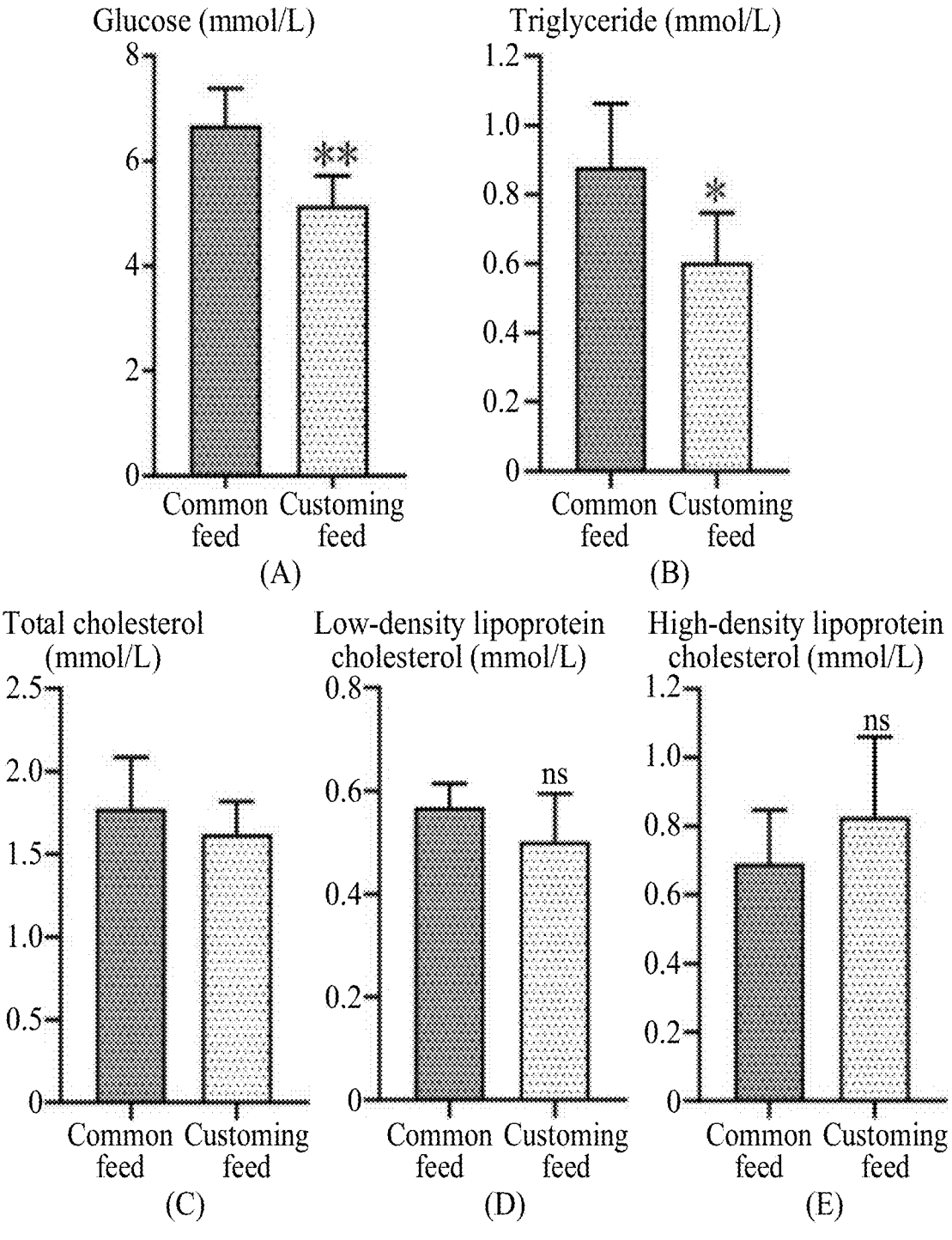
Figure 49:
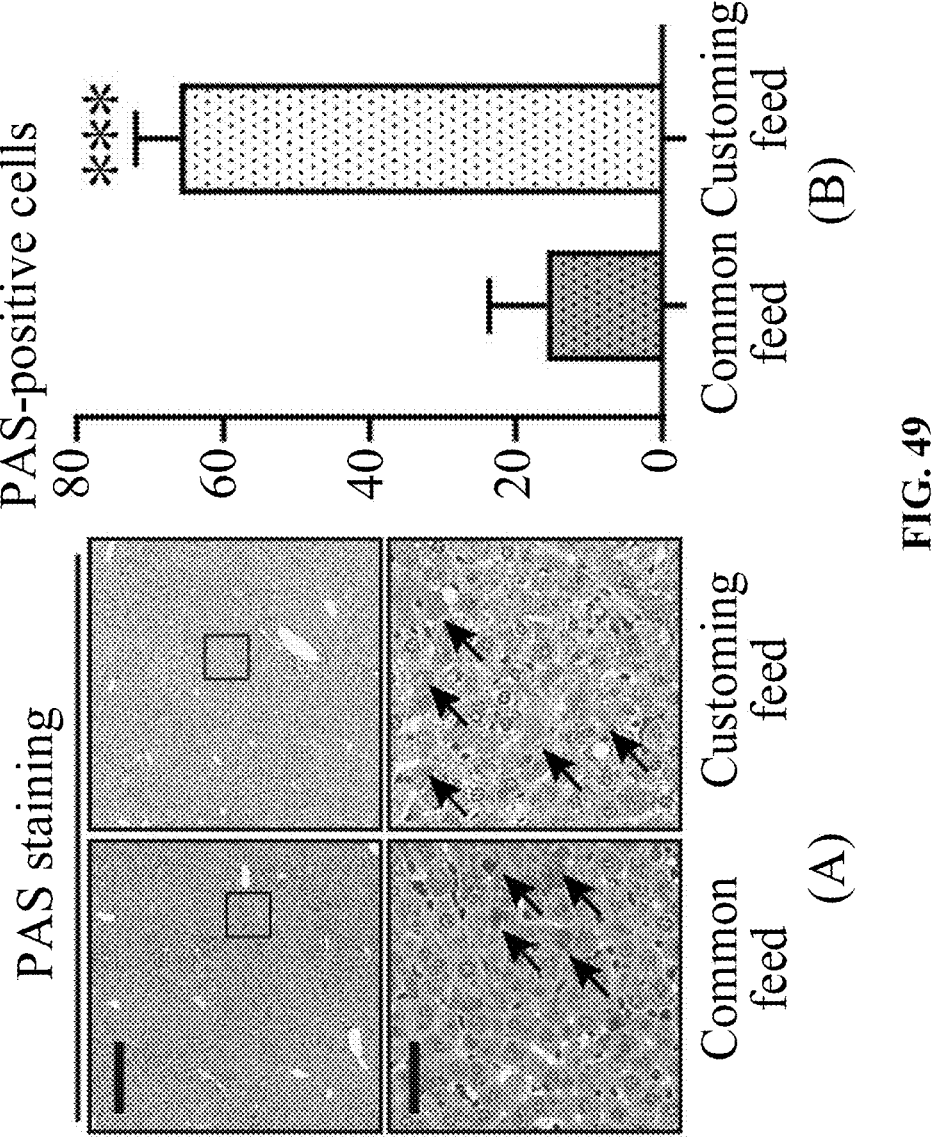
Figure 50:
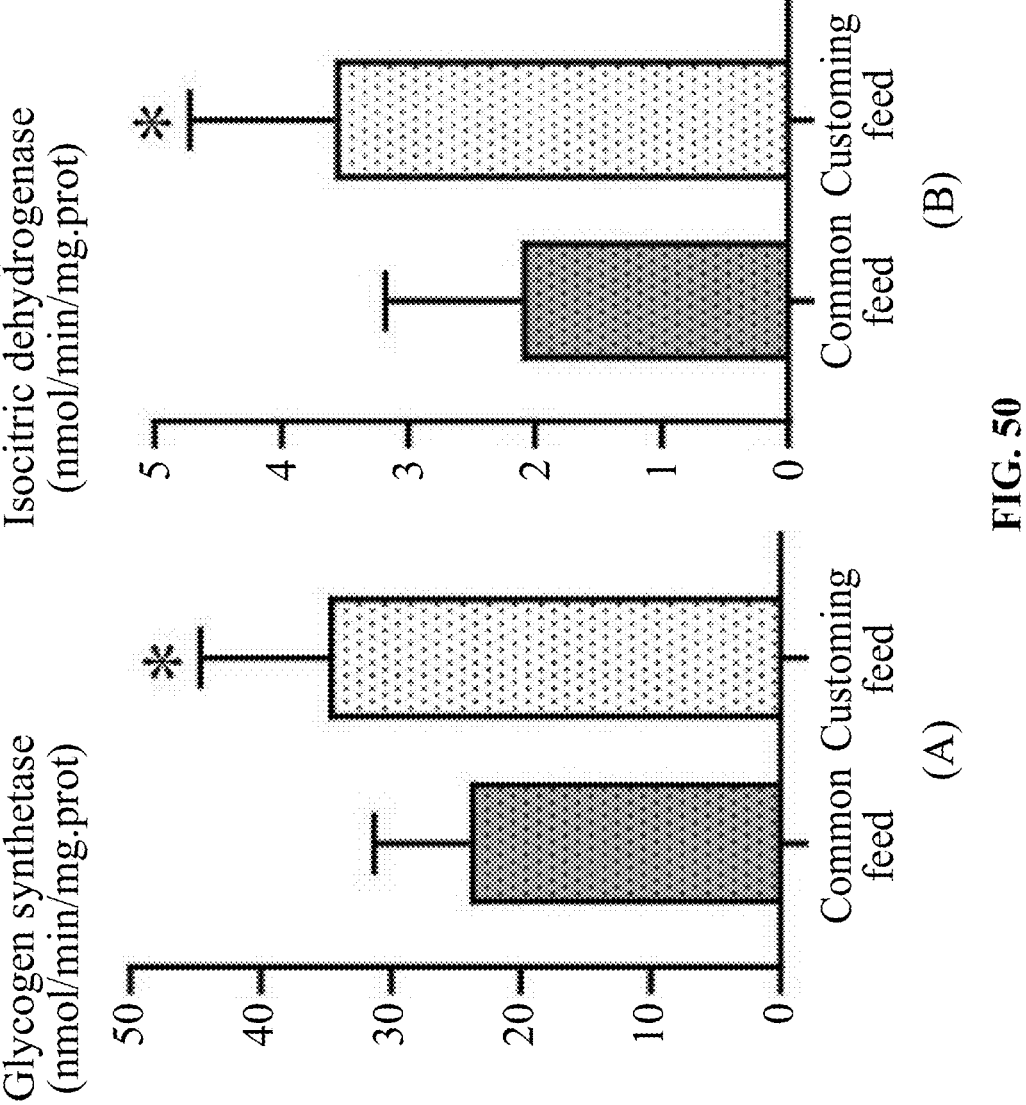
Figure 51:
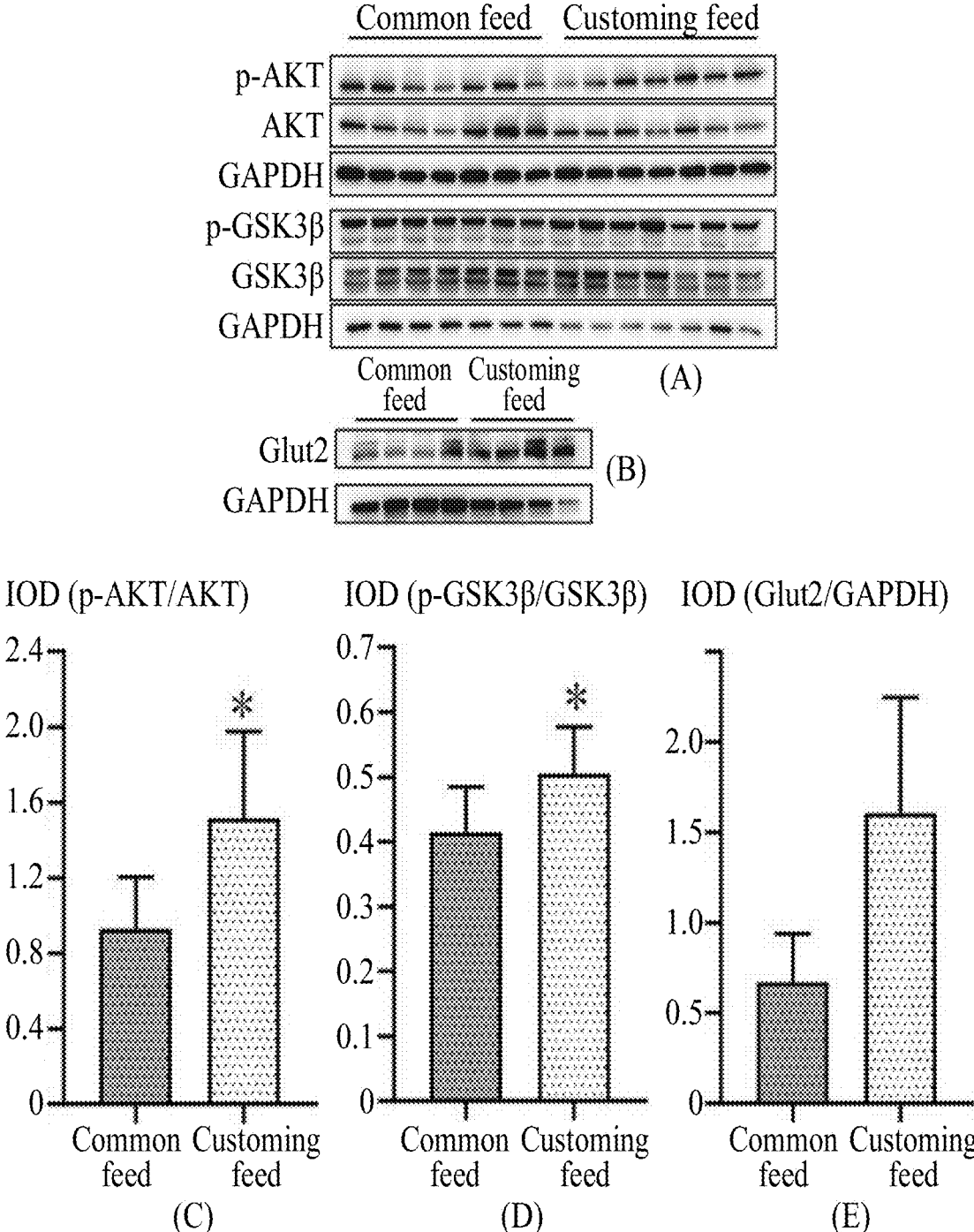
Figure 52:
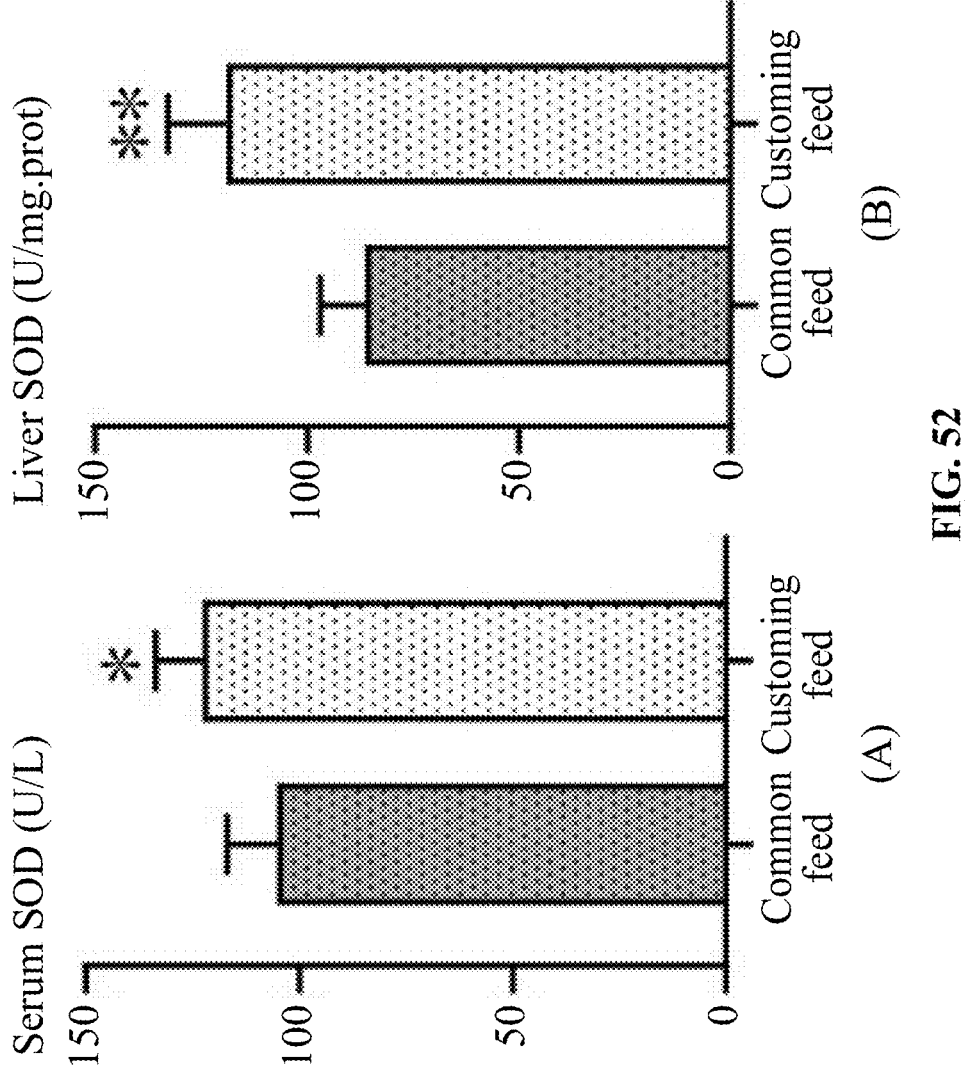

and common feed in Example 13 of the disclosure; wherein the arrow represents inflammatory cell infiltration;

FIG. 48 shows a decrease in the serum glucose and triglyceride of naturally aging mice (24 months old) fed with test feed (containing 2 g/kg of compound JAC-4) in accordance with Example 13 of the disclosure;

FIG. 49 shows a PAS staining demonstrating the liver of naturally aging mice (24 months old) fed with custom feed (containing 2 g/kg of compound JAC-4) and common feed in accordance with Example 13 of the disclosure; wherein the arrow represents the cells positive for PAS staining indicating glycogen accumulation;

FIG. 50 shows a change in the rate-limiting enzymes related to glucose metabolism in the liver of naturally aging mice (24 months old) fed with test feed (containing 2 g/kg of compound JAC-4) in accordance with Example 13 of the disclosure;

FIG. 51 shows the Western blot results of the AKT/GSK3β signaling pathway related to glucose metabolism in the liver and the glucose transporter protein Glut2 in liver tissue cell membranes of naturally aging mice (24 months old) fed with test feed (containing 2 g/kg of compound JAC-4) accordance with Example 13 of the disclosure; GAPDH is used as an internal reference protein;

FIG. 52 shows an increase in SOD in the serum and liver of naturally aging mice (24 months old) fed with test feed (containing 2 g/kg of compound JAC-4) in accordance with Example 13 of the disclosure.

DETAILED DESCRIPTION

To further illustrate the disclosure, embodiments detailing JWA gene and compounds and used thereof for preparing anti-aging products are described below. It should be noted that the following embodiments are intended to describe and not to limit the disclosure.

Unless otherwise specified, the operations involved in the methods are conventional, and the reagents and materials used are commercially available products. JWA gene has an accession number AF070523 in GenBank, and is represented by the sequence of SEQ ID NO: 1. JWA protein is coded by the JWA gene and is represented by the sequence of SEQ ID NO: 2.

Example 1

Expression of JWA protein in mouse liver and spleen decreased with advancing age.

The expression level of JWA protein in mouse tissues of different ages was detected to determine whether the JWA expression was associated with age.

Mice were euthanized at different ages (16, 19, 48 and 96 weeks old) and liver and spleen tissues were collected, and frozen at -80° C. The total protein of the liver and spleen tissues was extracted with a mixture of tissue lysate and protease inhibitors, and separated by electrophoresis through 12.5% polyacrylamide gel. The protein bands of 20-25 kDa were cut out of the polyacrylamide gel according to a protein molecular weight marker, and transferred from the polyacrylamide gel onto a polyvinylidene fluoride (PVDF) membrane. Thereafter, the JWA protein was imprinted with a mouse anti-JWA antibody and a horseradish peroxidase (HRP)-goat anti-mouse IgG antibody. The expression level of JWA protein was then determined by HPR substrate and a chemiluminescent device.

Figure 1:
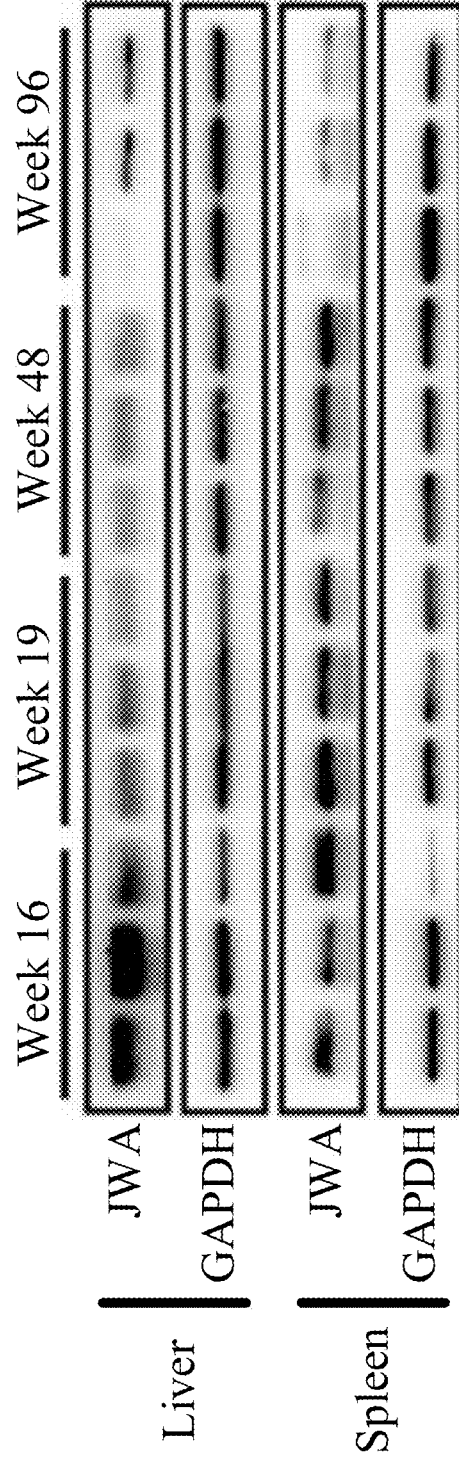
FIGS. 1-3 are protein gel staining showing expression levels of JWA protein in the liver and spleen tissues of mice of different ages in accordance with Example 1 of the disclosure; GAPDH is used as an internal reference protein.
Figures 2, 3:
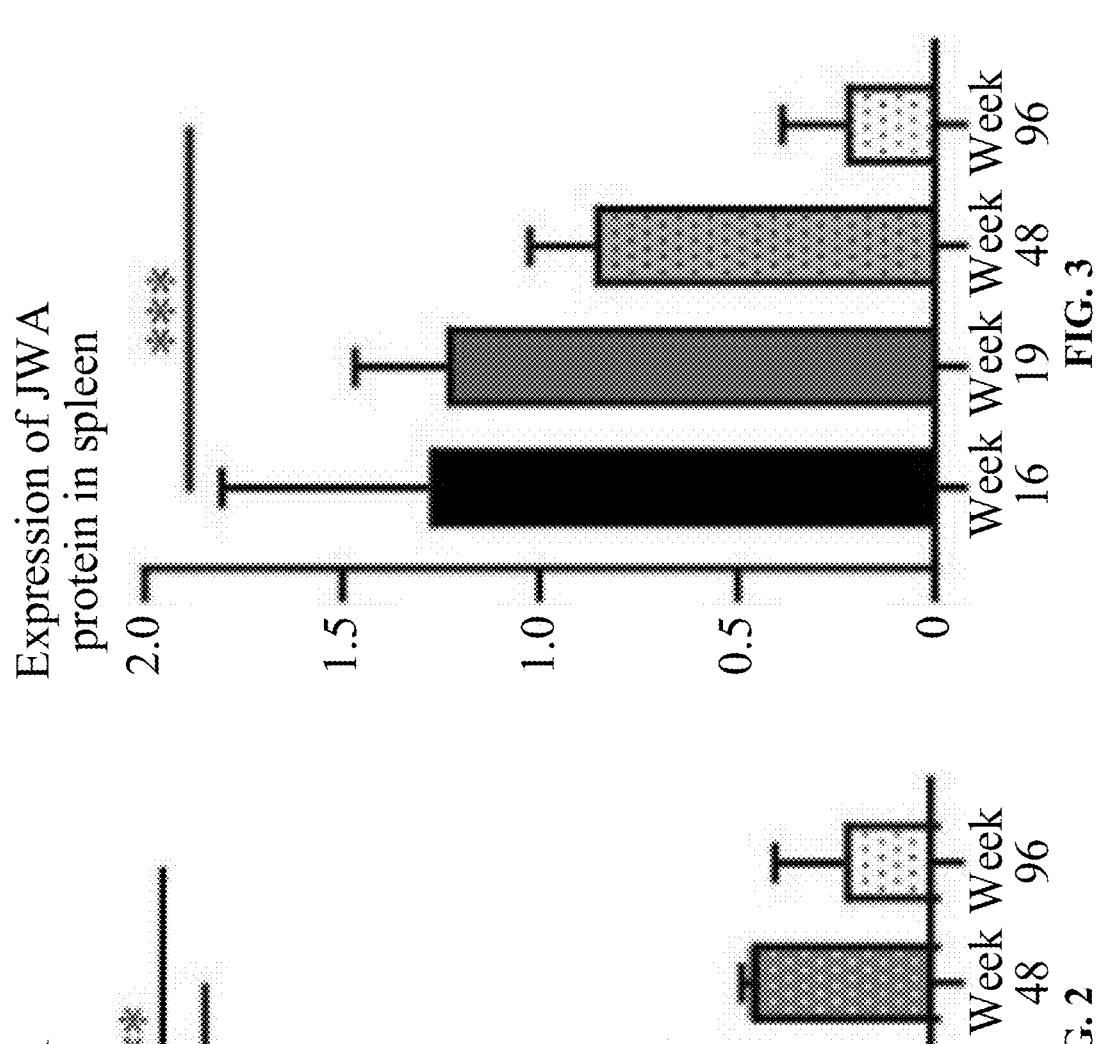

As shown in results of FIGS. 1-3, the expression level of JWA protein in the liver and spleen tissues gradually decreased with advancing age of mice.

Example 2

Knockout of JWA gene in mice leads to weight loss and life shortening.

Wholly-body JWA gene knockout mice were created using a Cre-loxp recombinase system and used to analyze the relation of JWA gene to weight loss and life shortening.

Figures 4, 5:
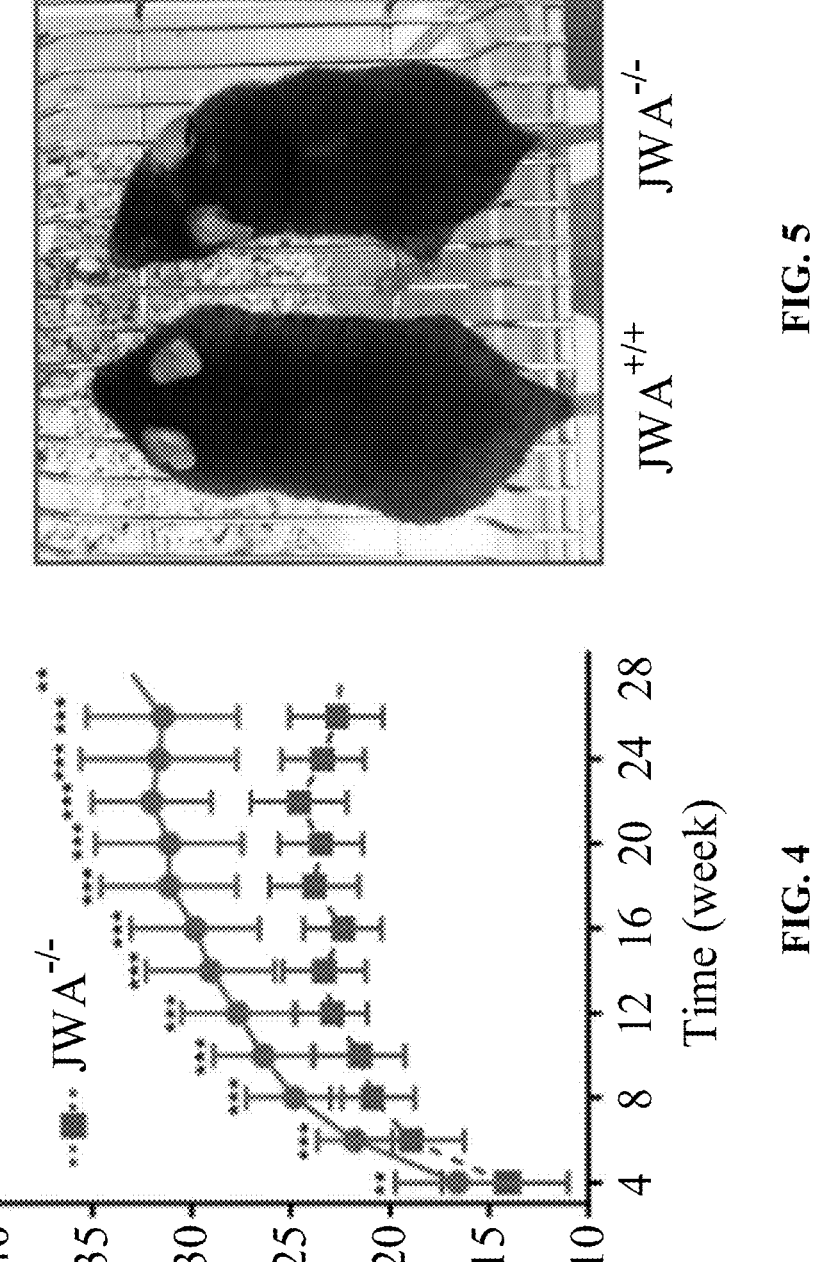
FIG. 4 shows body weight curves of JWA$^{-/-}$ mice and wild-type mice in accordance with Example 2 of the disclosure.
FIG. 5 is an image illustrating the appearance of JWA$^{-/-}$ mice and wild-type mice in accordance with Example 2 of the disclosure.
Figure 6:
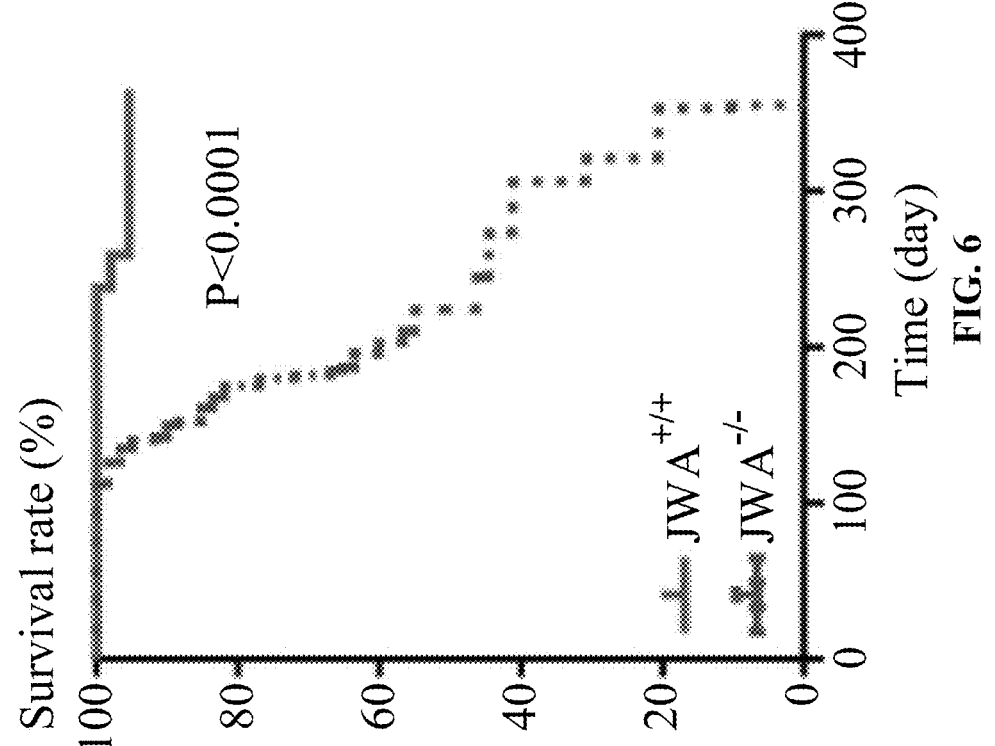
FIG. 6 shows survival curves of JWA$^{-/-}$ mice and wild-type mice in accordance with Example 2 of the disclosure.
Figures 7, 8:
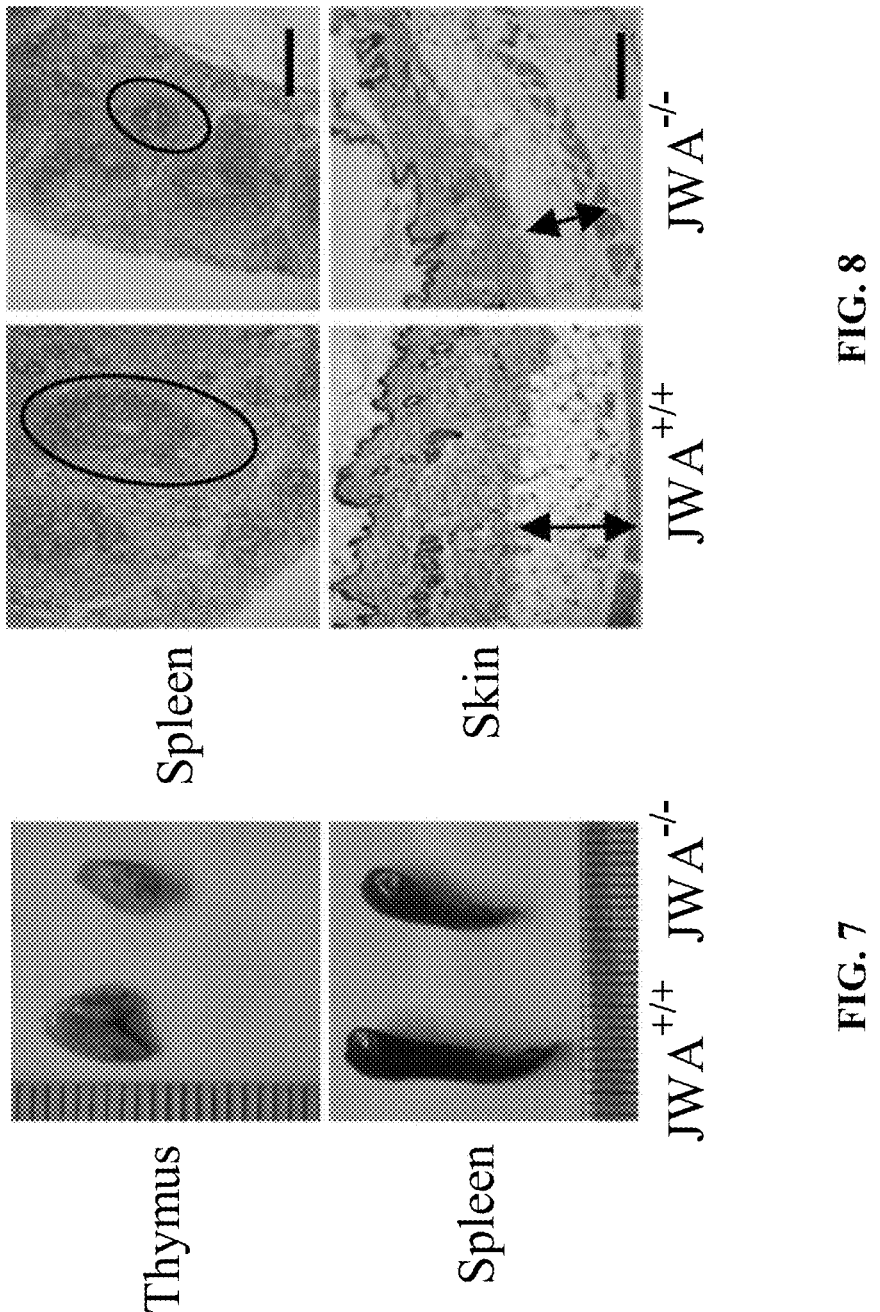
FIGS. 7-10 are images illustrating the phenotype of the aging tissues and organs of JWA$^{-/-}$ mice and wild-type mice in Example 3 of the disclosure.
Figure 9:
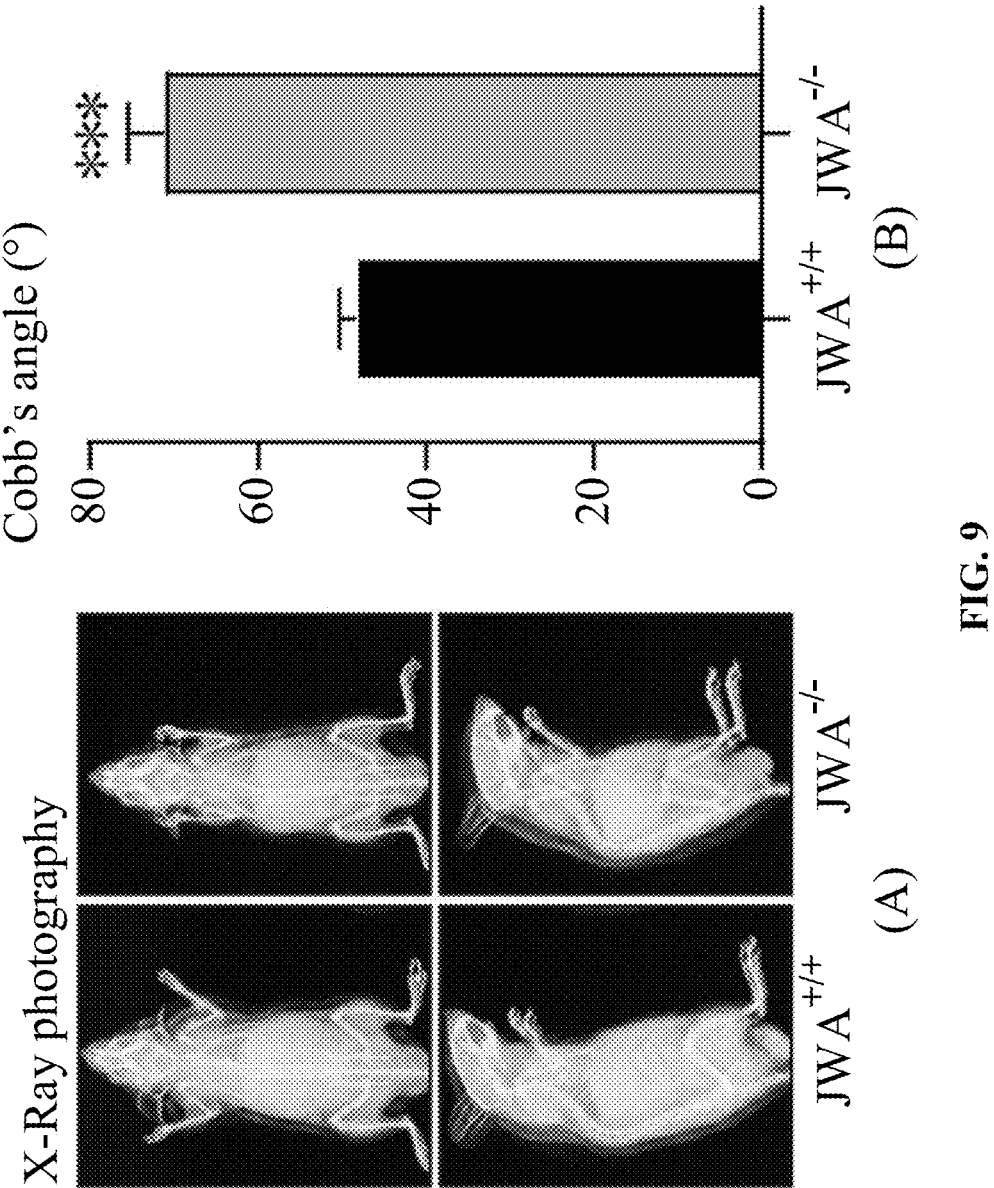
Figure 10:
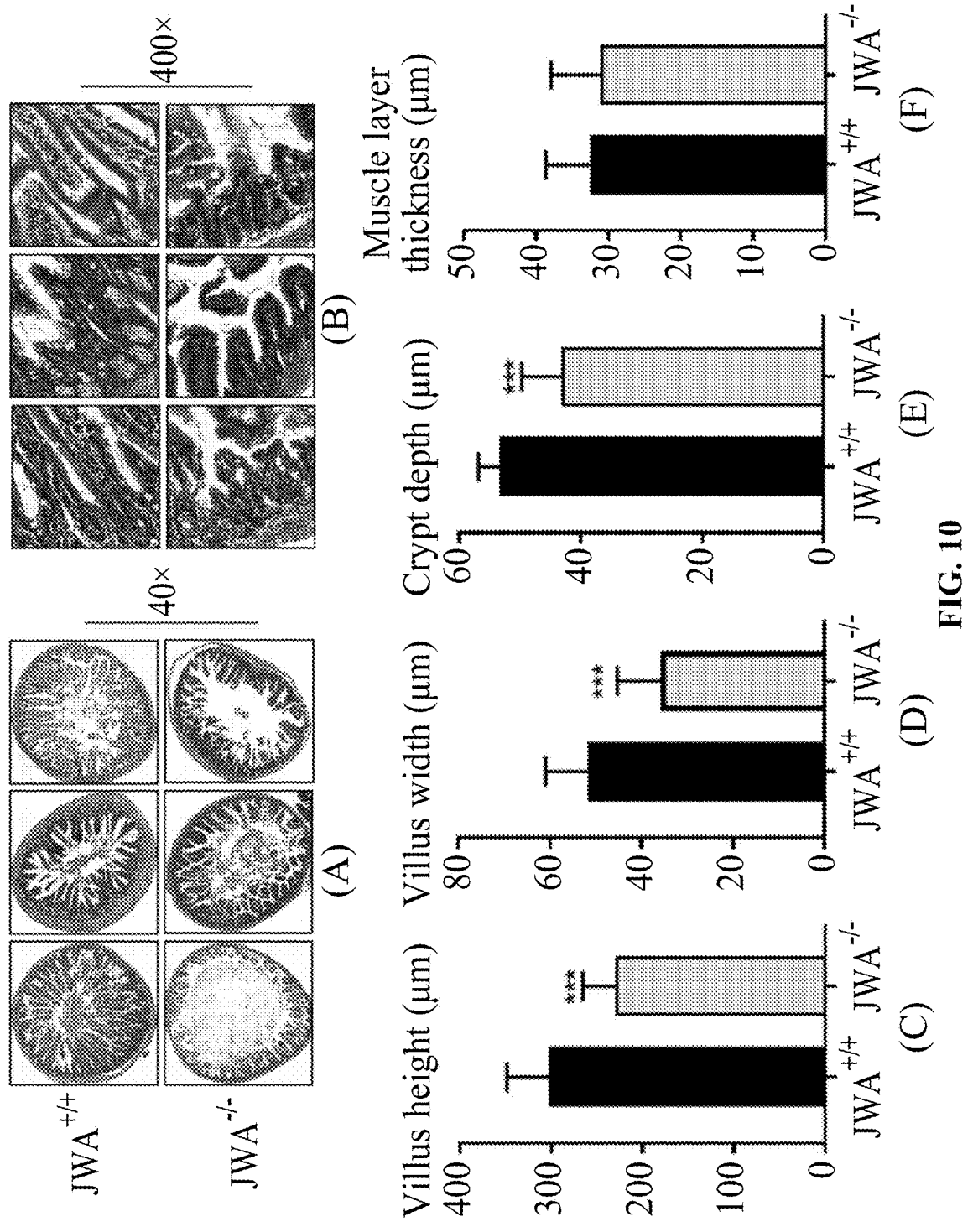

927 mice were continuously monitored for a prolonged period of time, including 215 homozygous ($JWA^{-/-}$) mice, 236 wild-type ($JWA^{-/-}$) mice, and 476 heterozygous ($JWA^{-/-}$) mice. Obvious ageing phenotype occurred in 90.7% (195/215) of homozygous mice and 4.2% (20/476) heterozygous mice. Referring to FIGS. 4-6, from the 4th week after birth (first detection), the homozygous mice had significantly lower body weight and longevity than the wild-type mice. The homozygous mice had a median survival time of 5.8 months (ranging from 1.4-11.8 months), while the wild-type mice had a median survival time of 2.5 years (30 months).

Example 3

Knockout of JWA gene in mice leads to aging phenotypes in tissues or organs.

Referring to Example 2, about 90.7% of the homozygous JWA knockout mice had significantly lower body weight and longevity than the wild-type mice, and also showed degeneration of both tissues and organs which results in loss of physical function and death. In this embodiment, at 6 months of age, gross morphology was observed in the homozygous JWA knockout mice and wild-type mice using the methods comprising hematoxylin-eosin (HE) staining for tissue section and X-ray imaging, etc. Referring to FIGS. 7-10, the JWA knockout mice produced obvious aging phenotypes in tissues and organs, such as immune organ atrophy, skin atrophy, bone deformity, as well as atrophy of villi and crypt of small -intestinal mucosal epithelium.

Example 4

Knockout of JWA gene leads to aging phenotypes of cells.

Cell senescence is the basis of tissue and organ senescence. In this embodiment, at 6 months of age, the liver tissue of $JWA^{-/-}$ mice and wild-type mice were sectioned and stained with senescence-associated β-galactosidase (SA-β-gal). A Real-Time PCR (RT-PCR) assay was performed to determine the relative telomere length in liver cells. The embryonic fibroblasts (MEFs) were extracted from the $JWA^{-/-}$ mice and wild-type mice, cultured in vitro, treated with hydrogen peroxide (H202) to induce cell senescence, and stained with SA-β-gal to visualize senescence cells. The liver cells were detected by flow cytometry to investigate the cell division cycle and the proportion of apoptotic cells. The number of cells was counted and used to calculate the cell doubling rate in each passage. The liver cells were analyzed by RT-PCR to determine the expression level of aging-related gene P21 in each passage.

Figure 11:
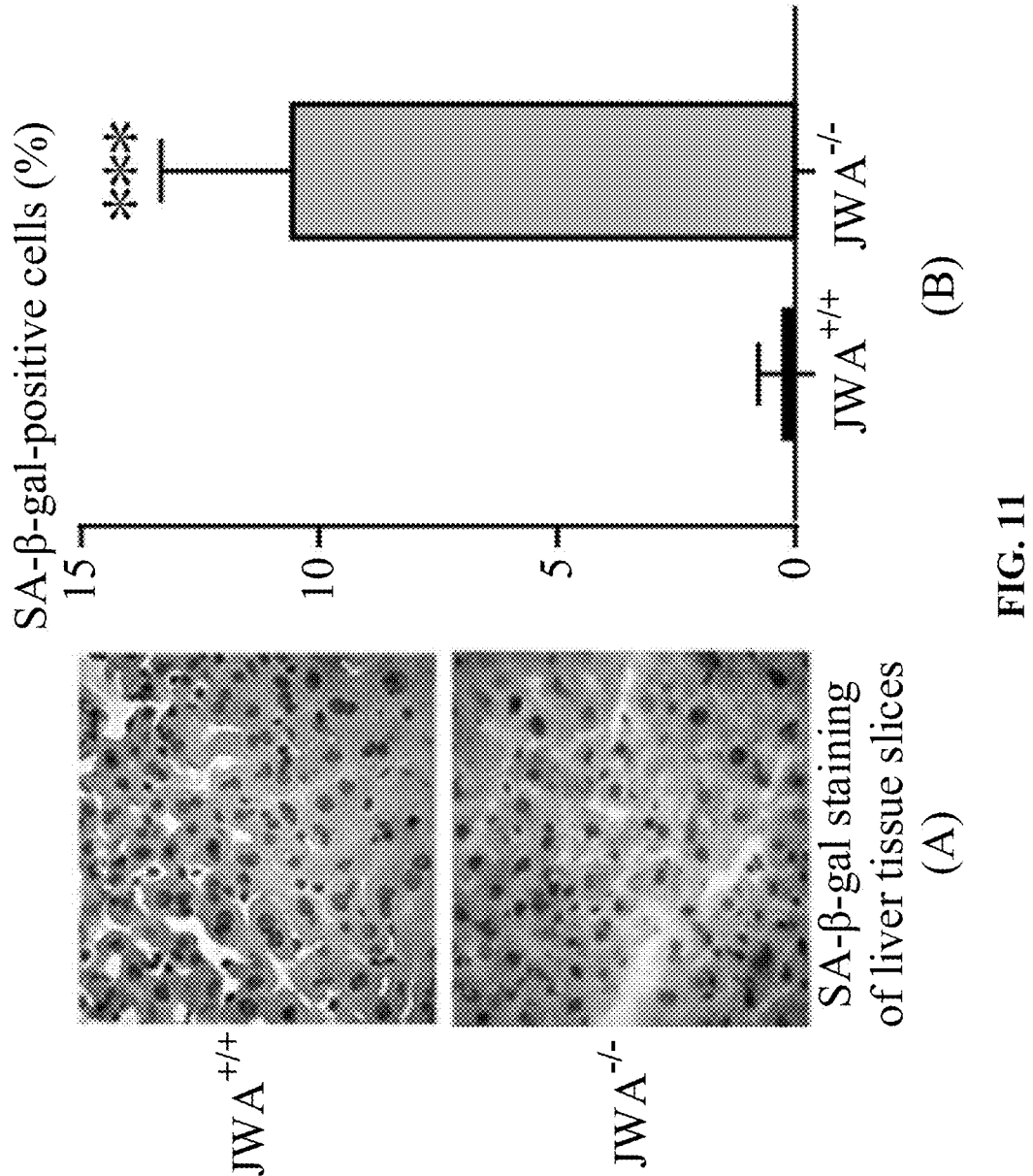
FIGS. 11-17 are images illustrating the aging-related phenotype induced by JWA knockout cells in accordance with Example 4 of the disclosure.
Figure 12:
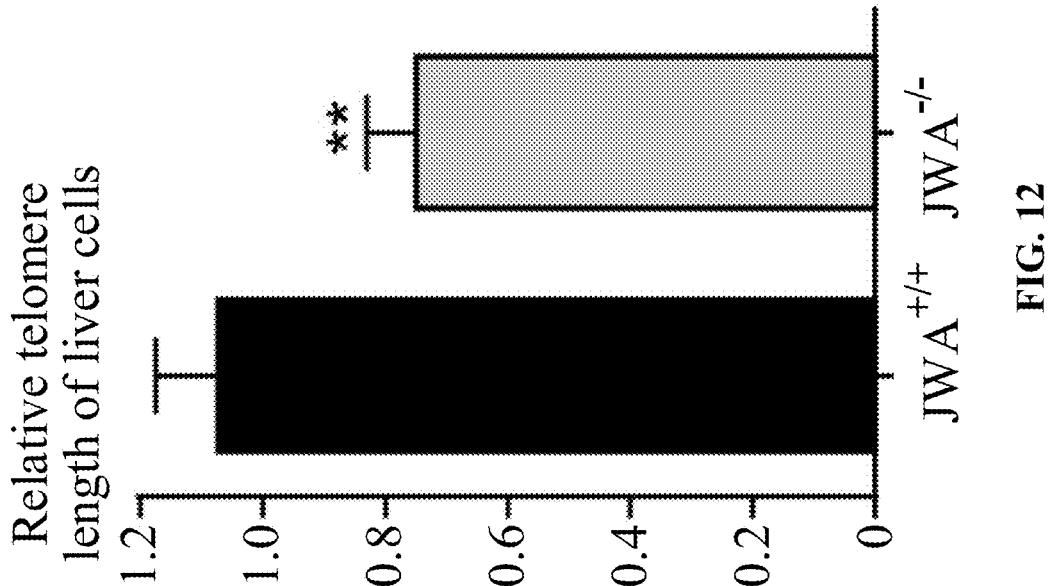
Figure 13:
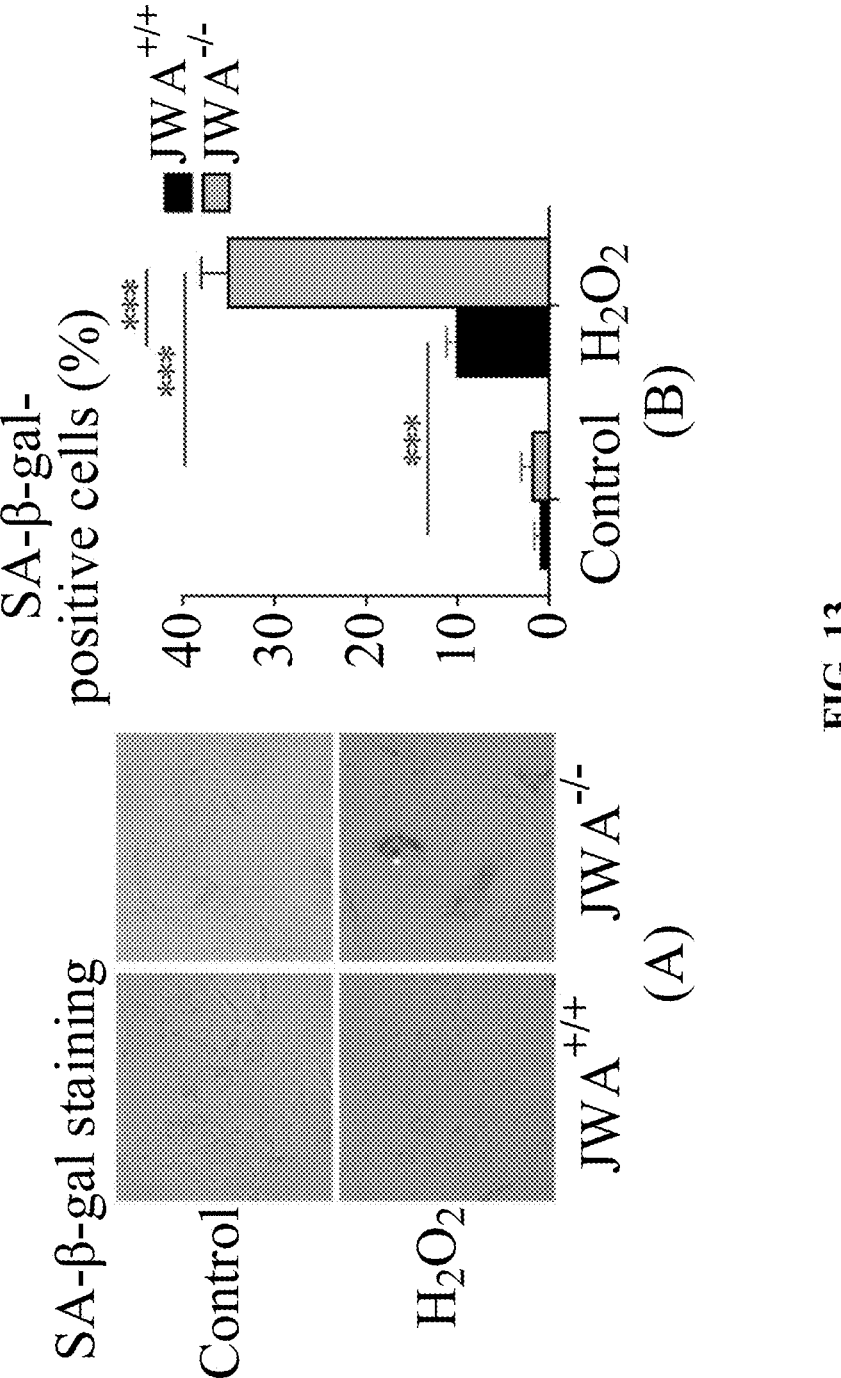
Figure 14:
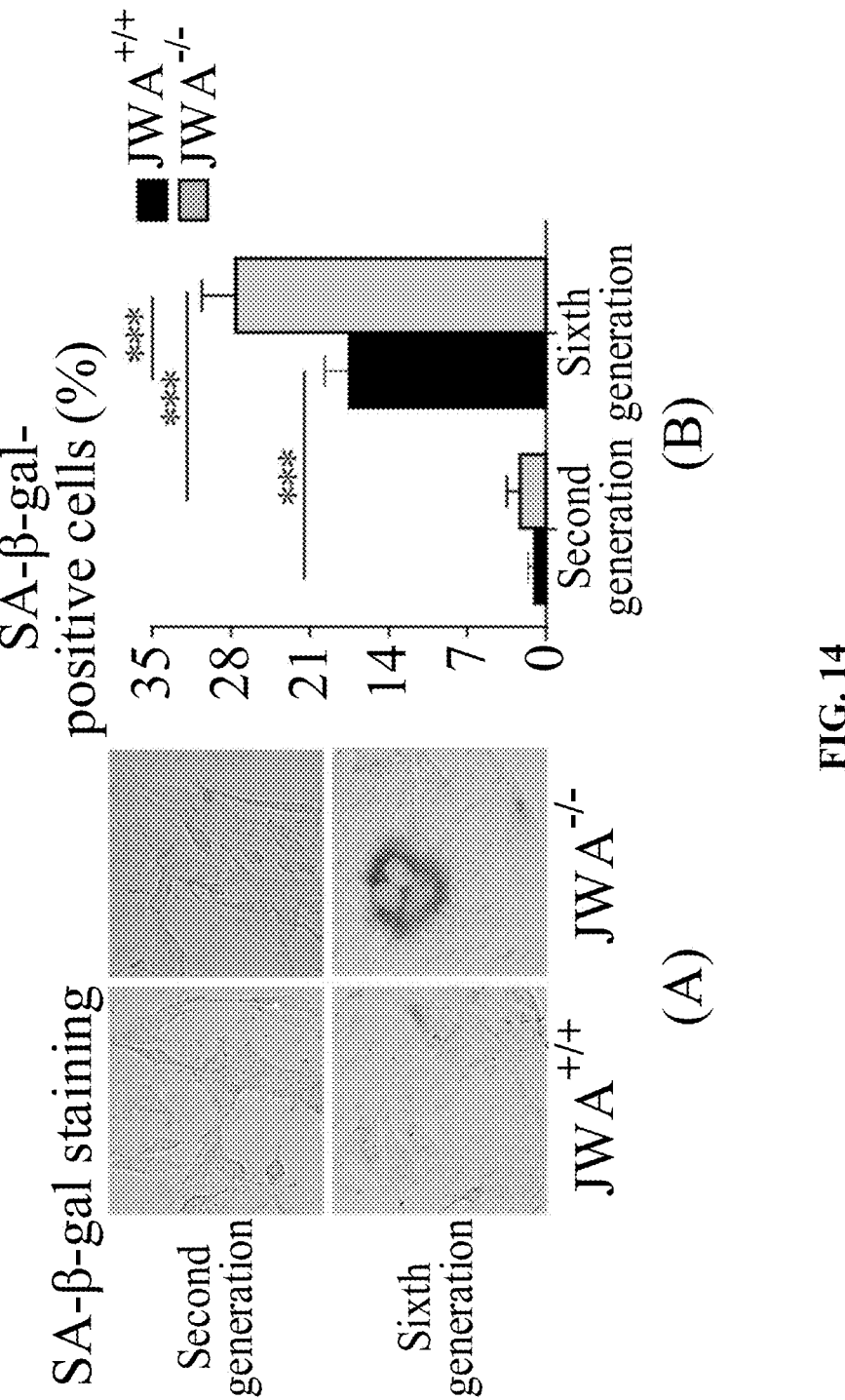
Figure 15:
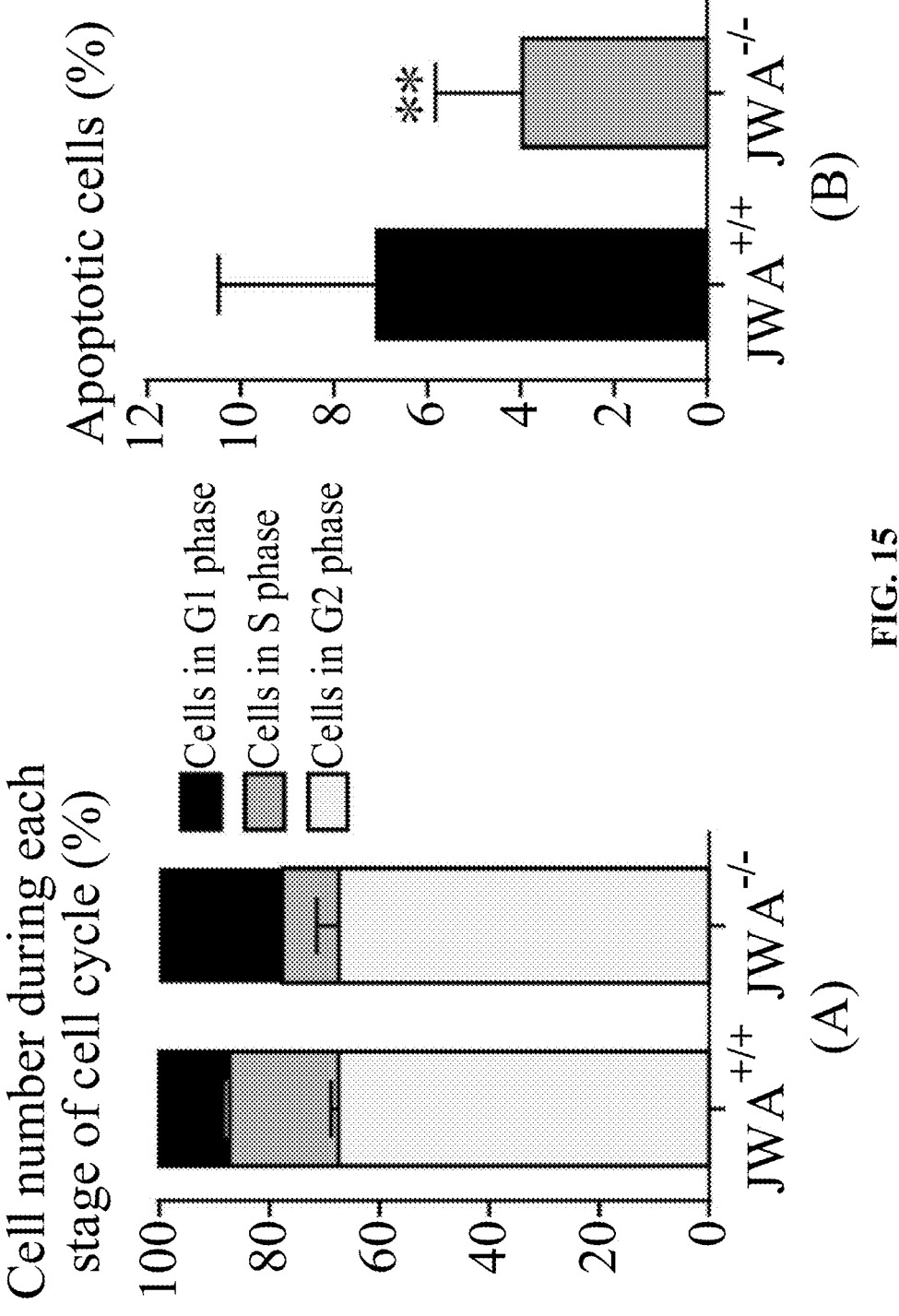
Figures 16, 17:
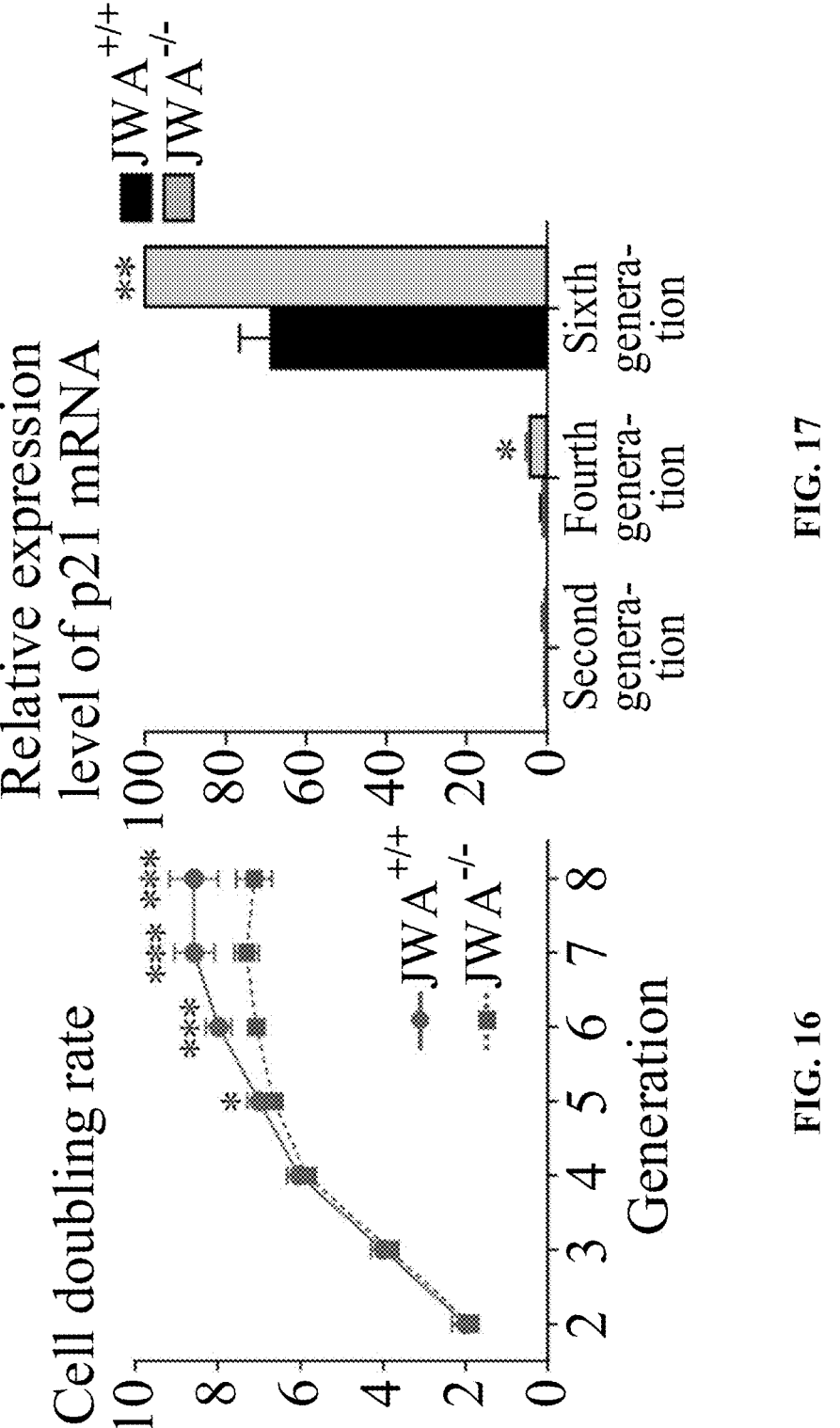
Figure 18:
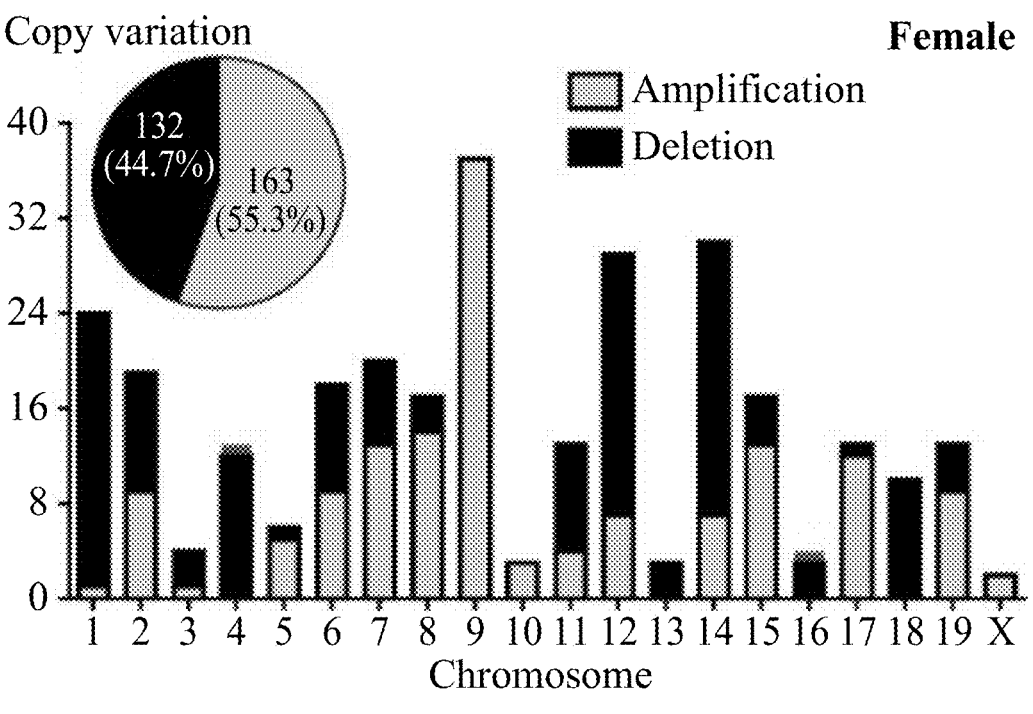
FIGS. 18-21 show increases in DNA copy number variation induced by JWA knockout liver cells in mice in accordance with Example 5 of the disclosure.
Figure 19:
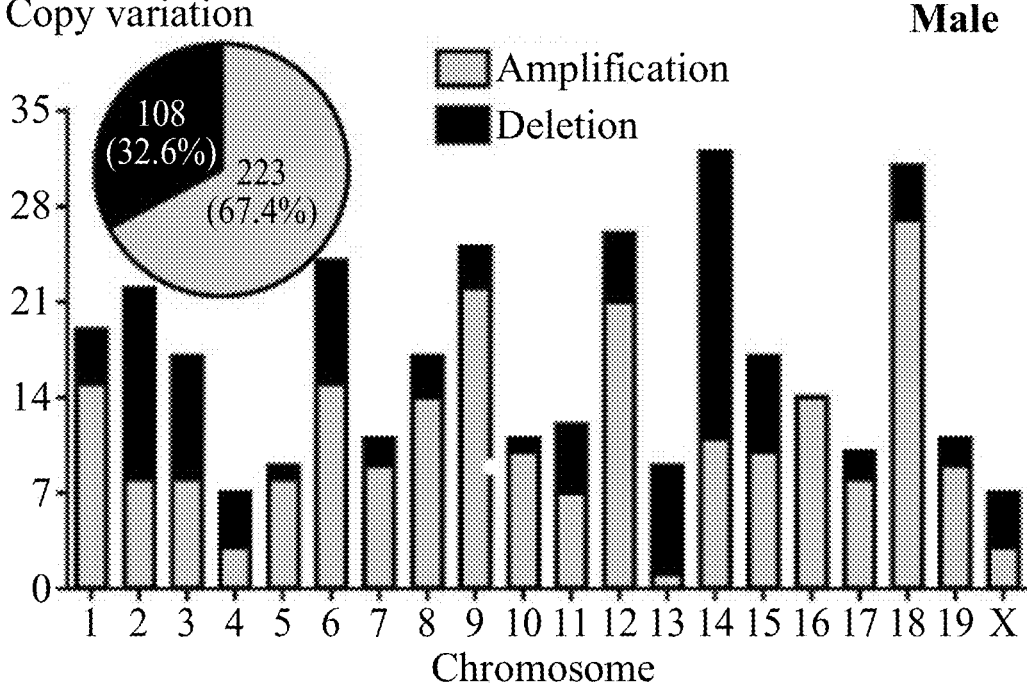
Figure 20:
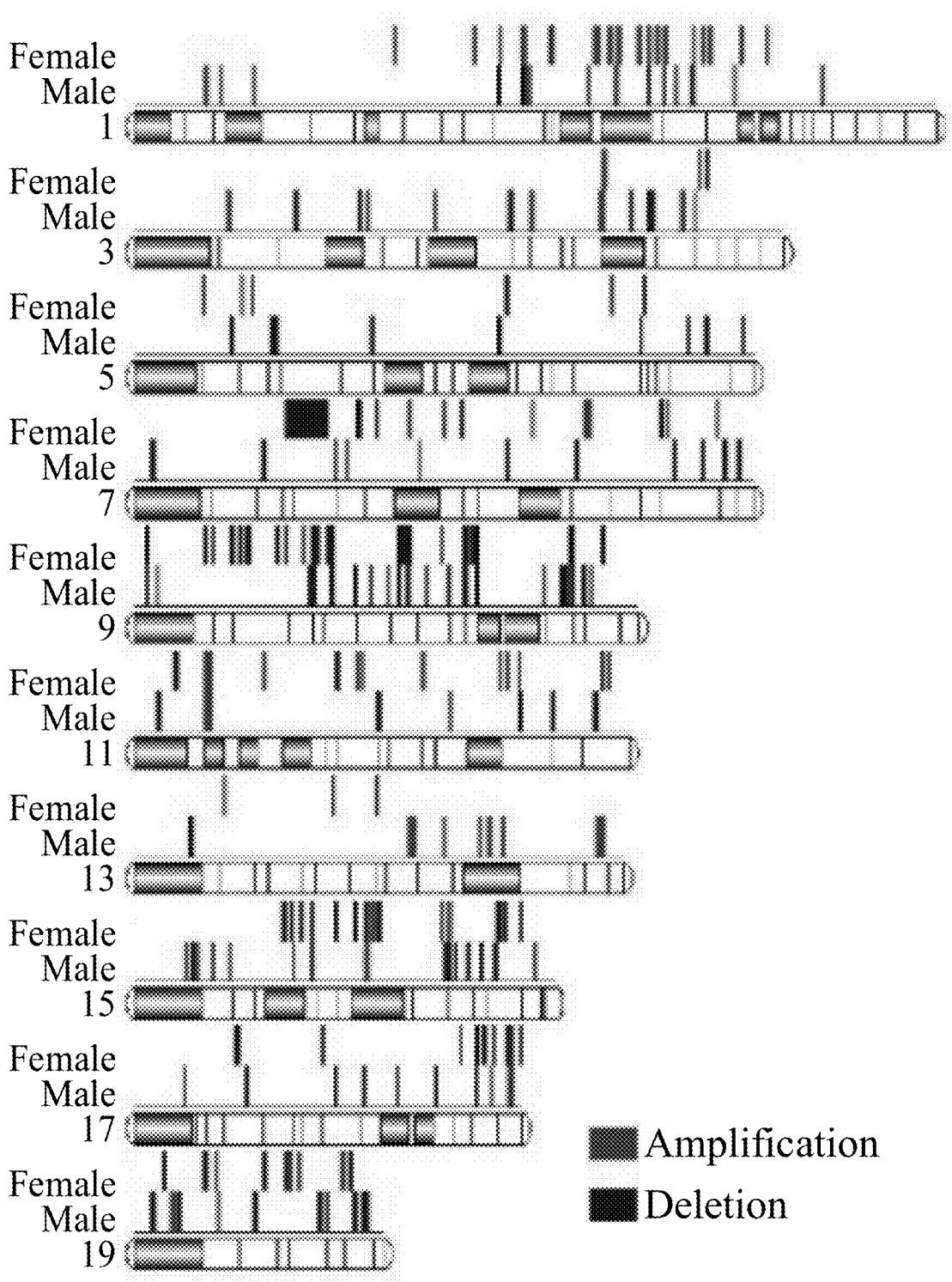
Figure 21:
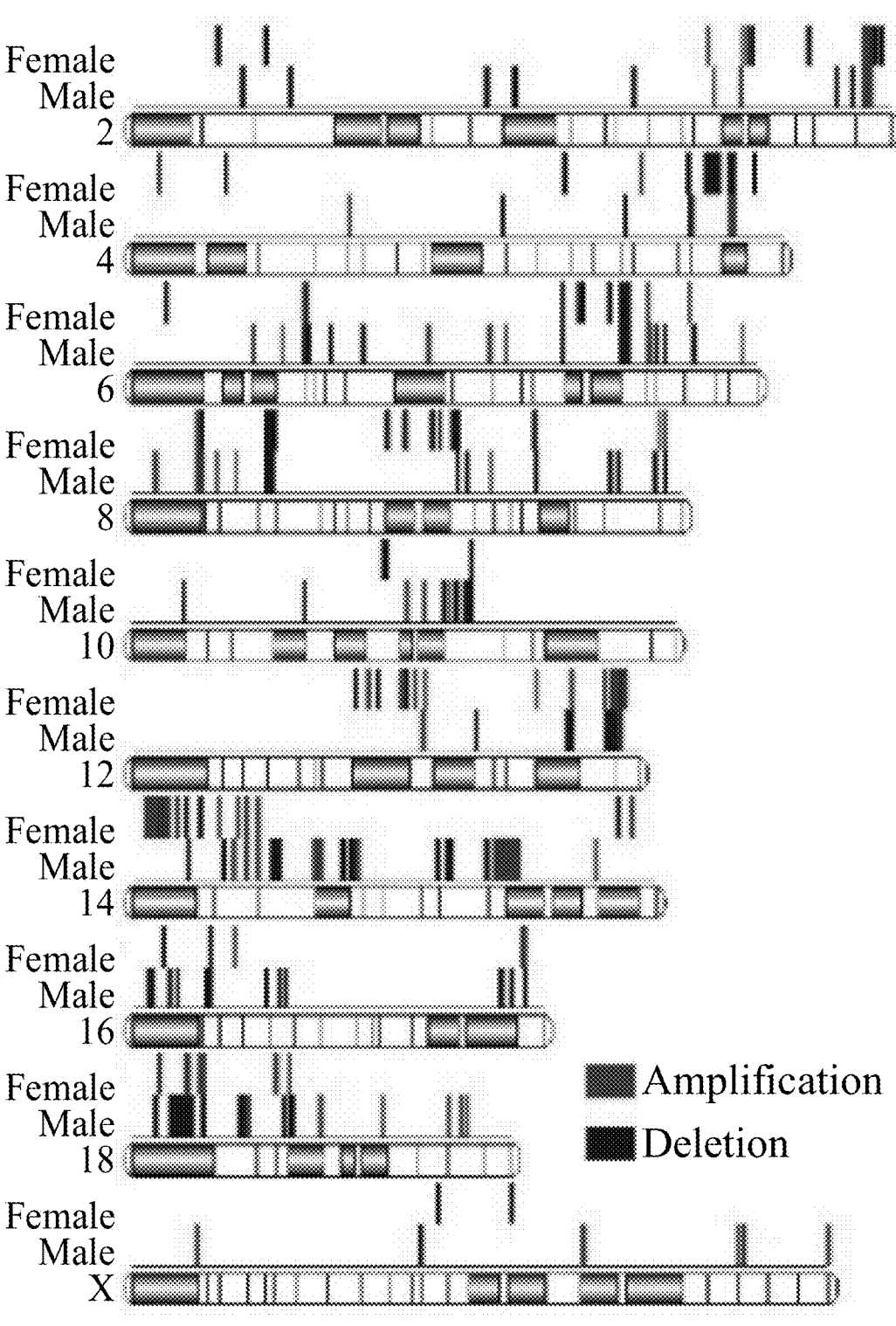

Referring to FIGS. 11-17, at 6 months of age, the liver tissue section of $JWA^{-/-}$ mice showed a significantly increase in the number of SA-β-gal positive stained cells compared with the wild-type mice (FIG. 11). The $JWA^{-/-}$ MEFs had a significantly shorter telomere length than the wild-type MEFs (FIG. 12). When stimulated by H202, the $JWA^{-/-}$ MEFs showed a marked increase in SA-β-gal positive staining compared with the wild-type MEFs (FIG. 13). With the generations passing, the $JWA^{-/-}$ MEFs also showed a marked increase in SA-β-gal positive staining compared with the wild-type MEFs (FIG. 14). The flow cytometry analysis indicated that $JWA^{-/-}$ MEFs showed a significant decrease in levels of cell division (DNA synthesis phase, S phase) and apoptotic cell death compared with the wild-type MEFs (FIG. 15), implying that more $JWA^{-/-}$ MEFs were maintained in a state of cell cycle arrest, which meant the cells were aging. With the generations passing, the $JWA^{-/-}$ MEFs had a cell doubling rate of significantly less than the wild-type MEFs (FIG. 16). The results of RT-PCR also showed that the aging-related gene p21 was expressed at a lower level in the $JWA^{-/-}$ MEFs compared with the wild-type MEFs (FIG. 17).

Example 5

Knockout of JWA gene leads to an increase in DNA copy number variation (CNV) in chromosomes in mouse liver cells.

CNV is also defined as one of signs of cellular senescence. In certain embodiment, the CNV in the chromosomes in the liver cells was detected with comparative genome hybridization microarray. Referring to FIGS. 18-21, the CNV (i.e. insertion or deletion) in the liver of the $JWA^{-/-}$ MEFs occurred more frequently than that in the wild-type MEFs.

Example 6

Knockout of JWA gene slows down the basal metabolic processes in the mice.

Basal metabolic abnormality is also defined as one of signs of cellular senescence. At 6 months old, the metabolic activity of $JWA^{-/-}$ mice and wild-type mice was measured using the TSE PhenoMaster system. The monitoring indictors include, but not limited to daily food intake, daily water intake, $O_2$ inhalation rate, $CO_2$ exhalation rate, exercise rate, and thermogenesis rate.

Figures 22, 23, 24:
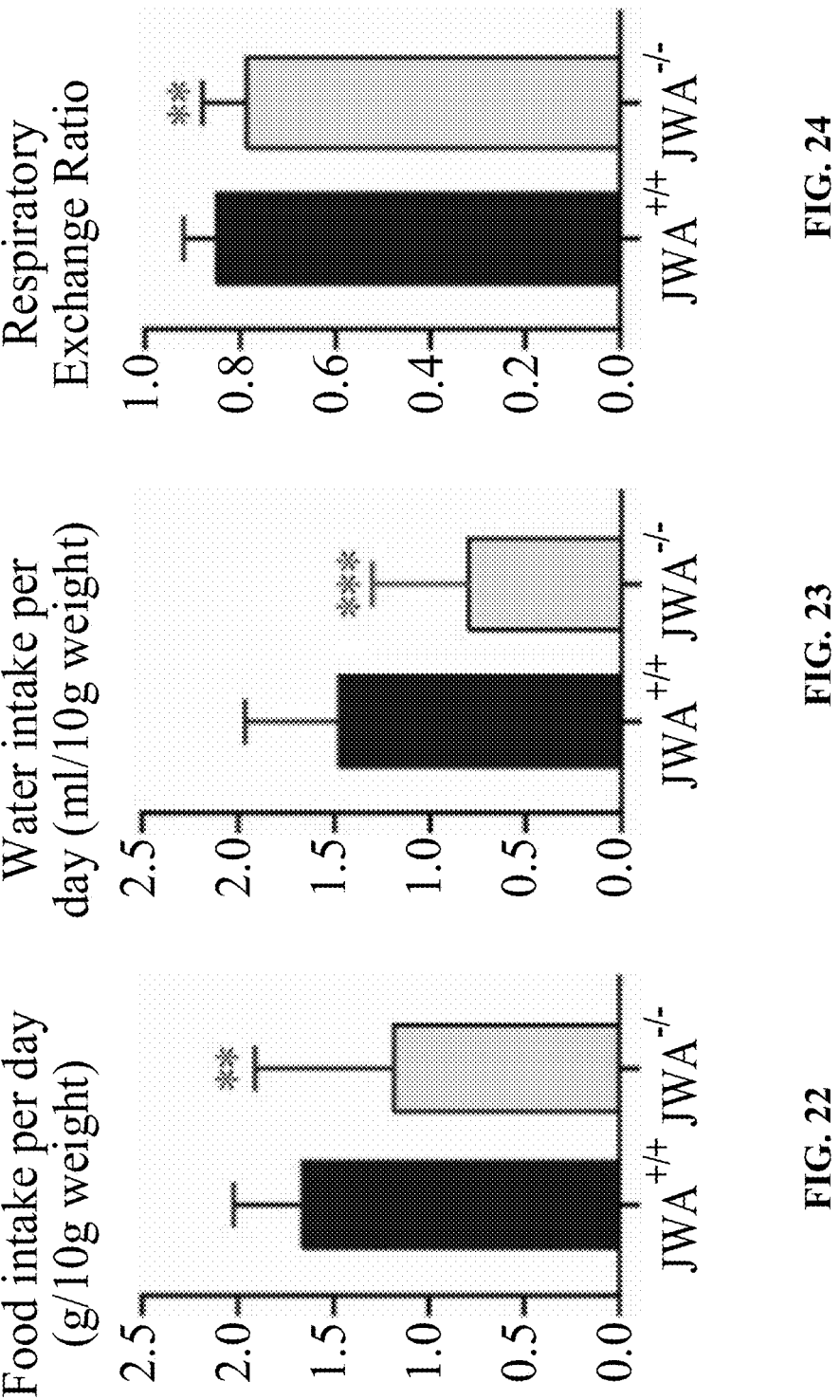
FIGS. 22-28 show decreases in basal metabolism induced by JWA knockout cells in mice in accordance with Example 6 of the disclosure.
Figures 25, 26:
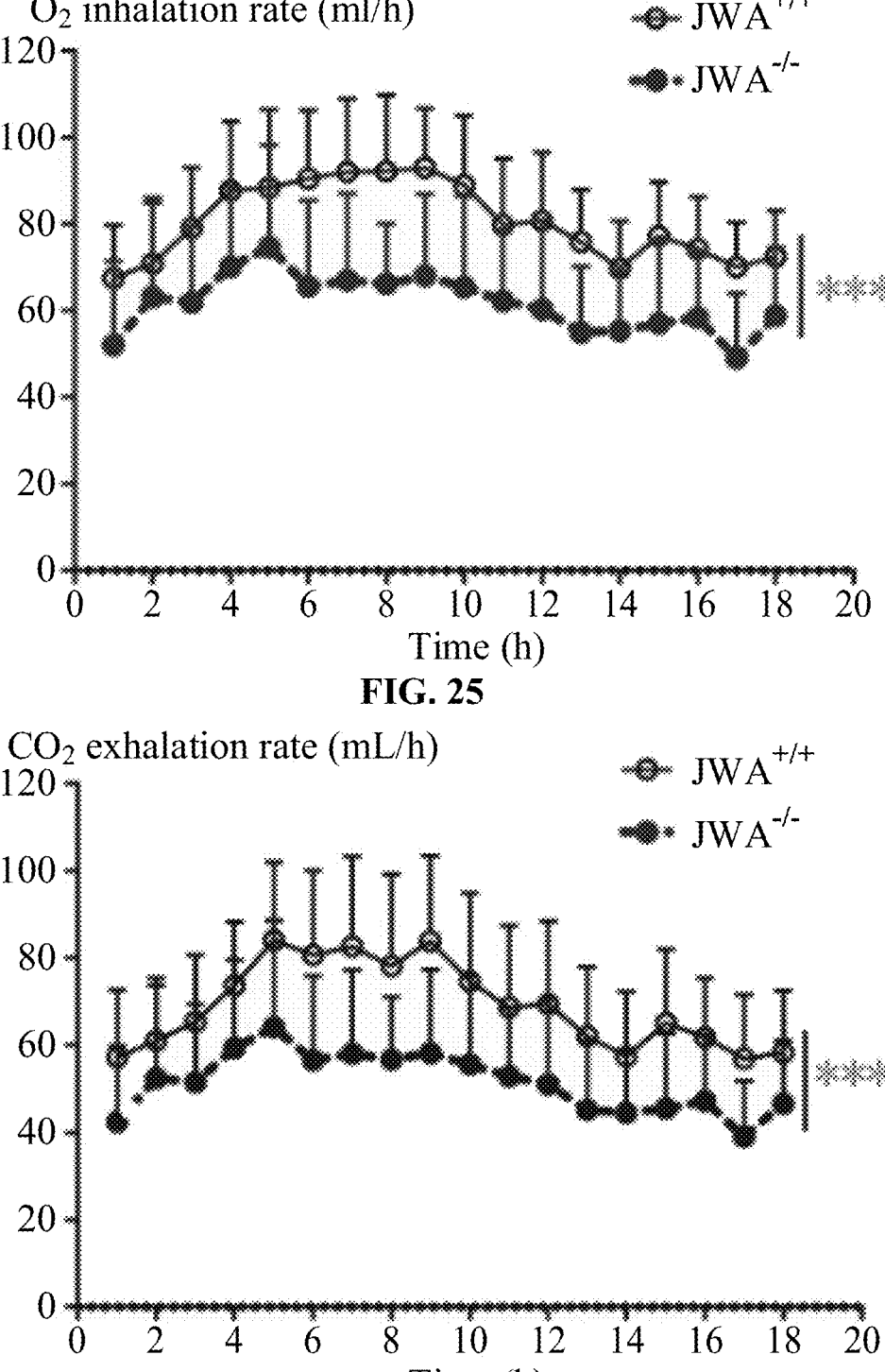
Figure 27:
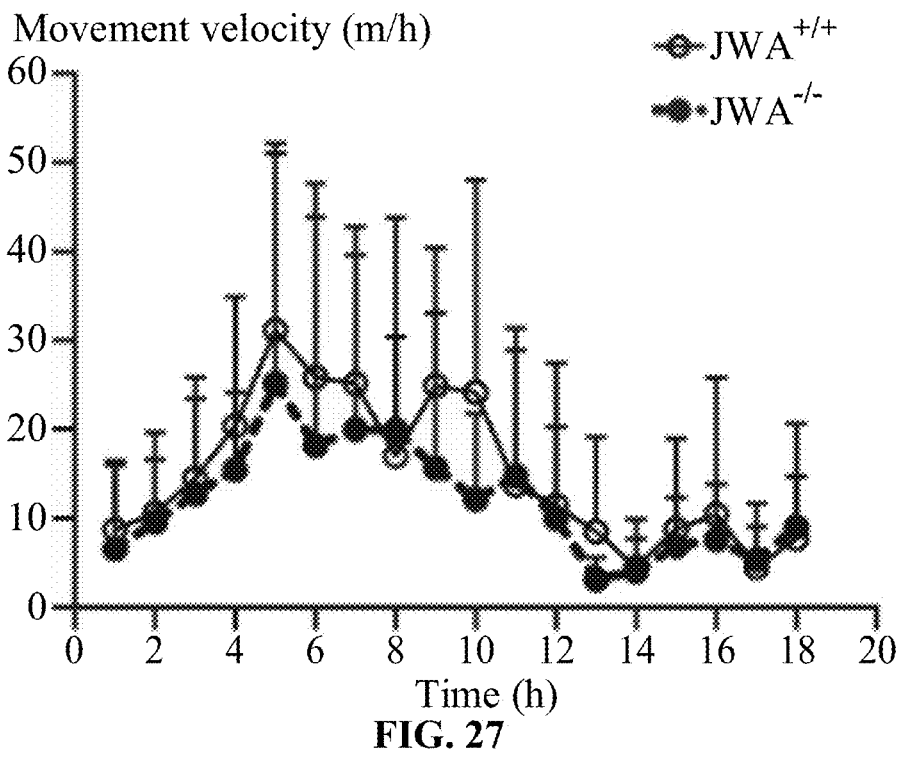
Figure 28:
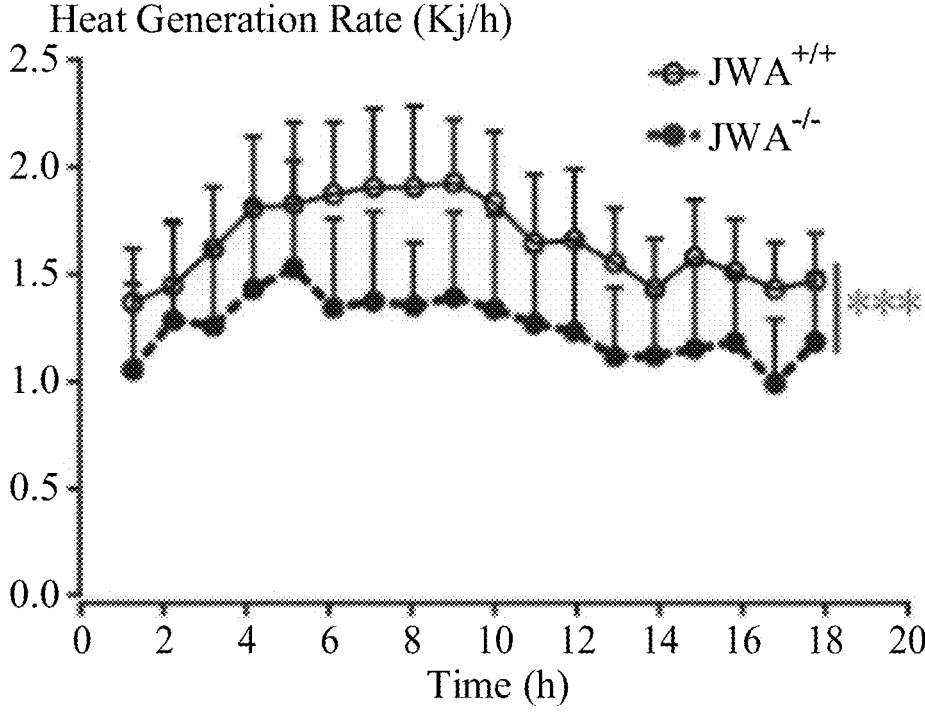
Figures 29, 30, 31:
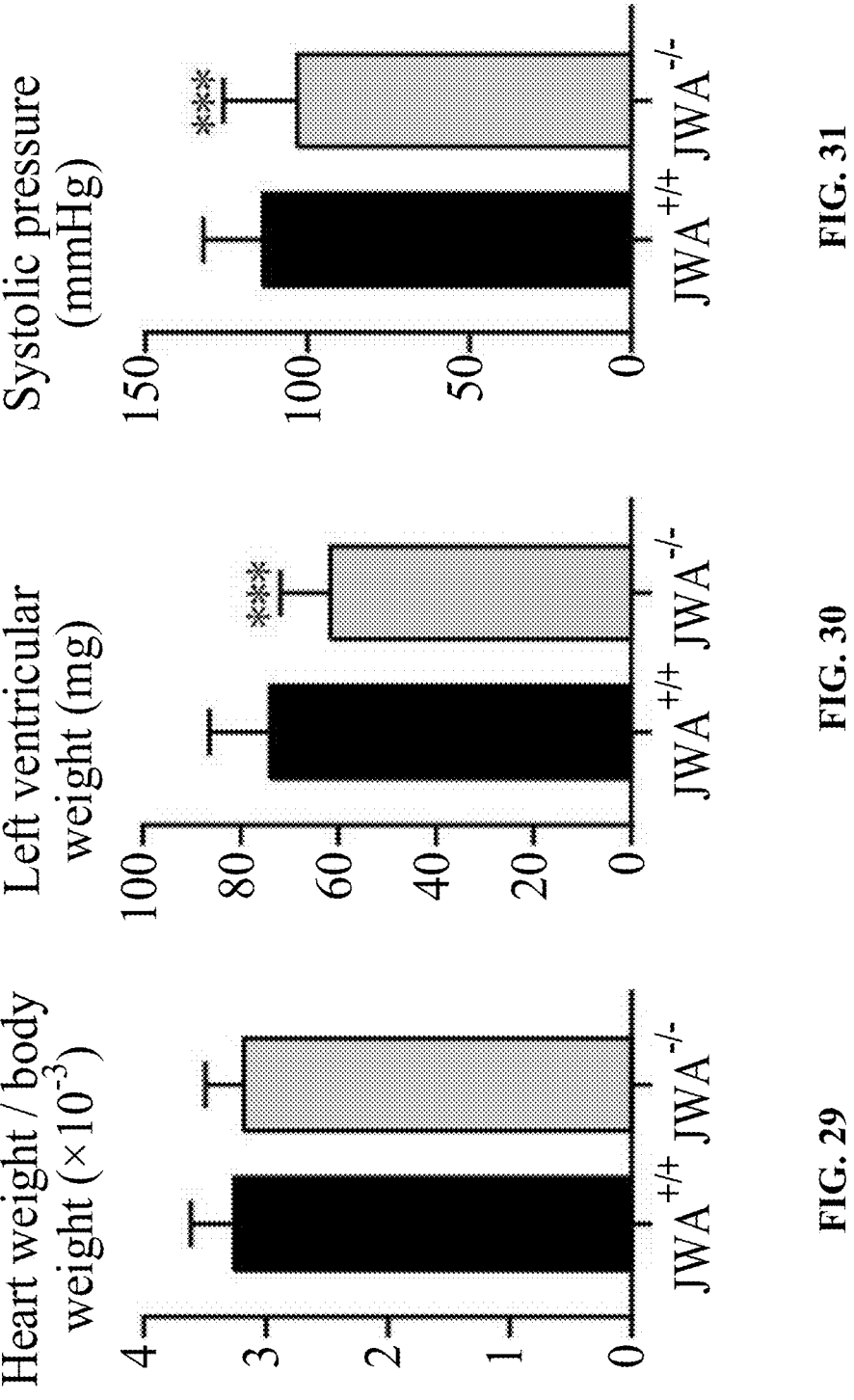
FIGS. 29-34 show changes in cardiovascular function induced by JWA knockout cells in mice in accordance with Example 7 of the disclosure.
Figures 32, 33, 34:
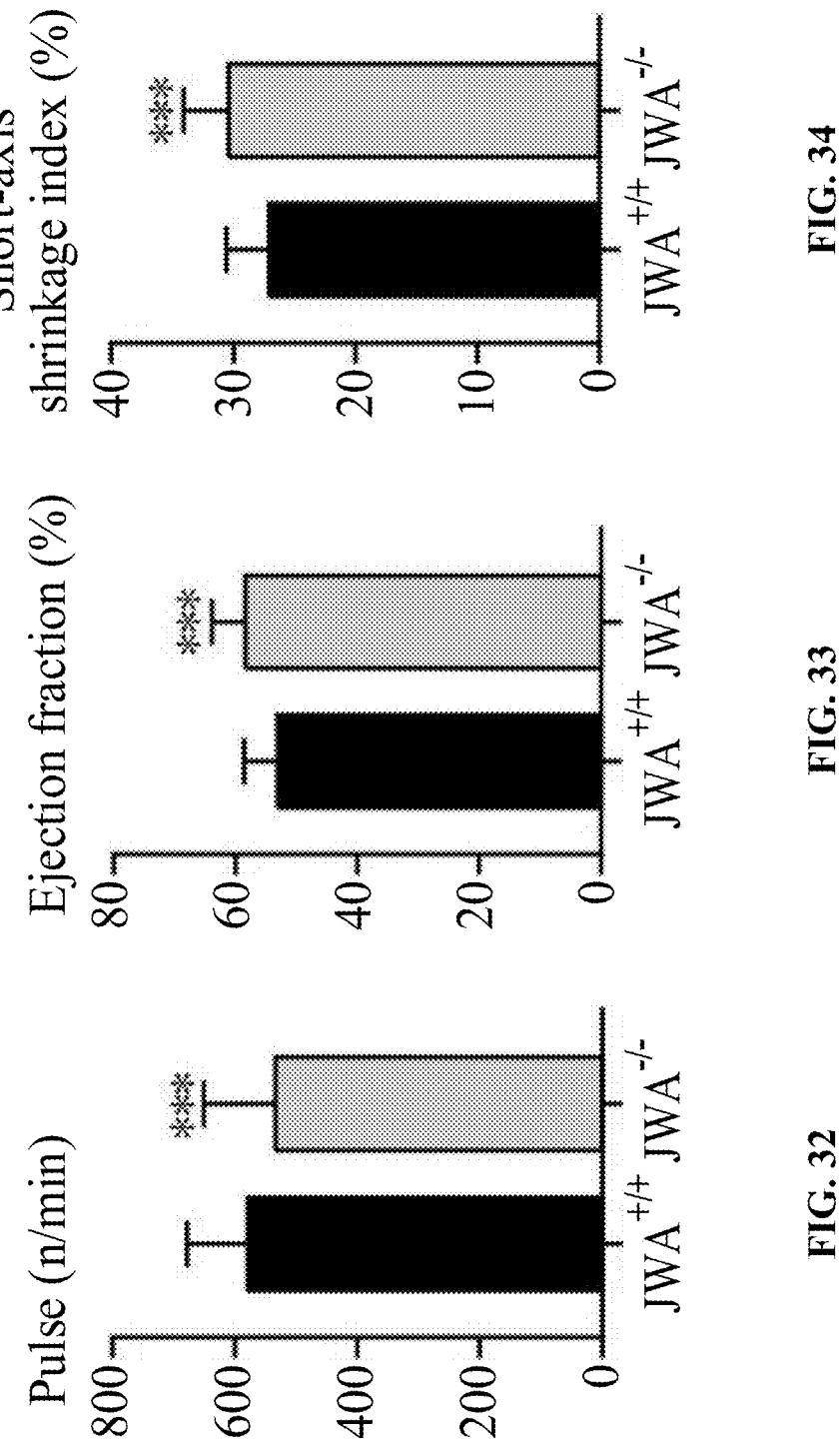

The results shown in FIGS. 22-28 indicate that the $JWA^{-/-}$ mice had a significantly lower basal metabolic rate than the wild-type mice, which is manifested in the decrease in the daily food intake (FIG. 22) and daily water intake (FIG. 23). The $JWA^{-/-}$ mice had a decreased respiration rate (FIG. 24), wherein the $O_2$ inhalation rate (FIG. 25) and $CO_2$ exhalation rate (FIG. 26) significantly decreased. Although no significant change in the exercise rate (FIG. 27), the heat production rate of the $JWA^{-/-}$ mice was significantly lower than that of the wild-type mice (FIG. 28).

Example 7

Knockout of JWA gene induced changes in the cardiovascular function of mice.

Aging is one of the major risk factors for chronic cardiovascular diseases. In certain embodiments, at 6 months old, A BP-2000 non-invasive blood pressure monitor was used to detect blood pressure and pulse rate in mice. Heart functions of mice were detected by Vevo 2100 Micro-Ultrasound, a small animal imaging system.

Referring to FIGS. 29-34, the $JWA^{-/-}$ mice showed no significant difference in the ratio of heart-weight to body weight (FIG. 29), but a significant decrease in left ventricular mass compared with the wild-type mice (FIG. 30), caused reduced systolic pressure (FIG. 31) and pulse rate (FIG. 32), and led to compensatory growth of the left ventricular ejection fraction (FIG. 33) and short-axis contraction (FIG. 34) in JWA$^{-/-}$ mice.

Example 8

Construction of a neomycin-resistant reporter plasmid containing JWA gene promoter.

The reporter vector plasmid containing JWA gene promoter was constructed and further used for screening compounds that encourage the expression of the JWA gene.

2012 bp upstream of the JWA transcription start site (referred to "JWA promoter sequence" hereafter) was amplified by RT-PCR according to the human-derived JWA promoter sequence (FIG. 35), and inserted into a pGL3-Neo vector by using KpnI and NheI restriction enzyme sites, thereby yielding a recombinant vector (FIG. 36) containing the JWA promoter sequence. The recombinant vector was transferred into *E. coli*. (DH5a). Positive clones were sequenced to verify accuracy, thereby obtaining a neomycin-resistant reporter plasmid containing the JWA gene promoter. The plasmid and corresponding strains were stored at −70° C. for use.

Example 9

Screening of regulatory molecules specific to JWA gene.

The JWA reporter gene assay was performed to screen the compounds that capable of activating the expression of the JWA gene.

Human bronchial epithelial (HBE) cells were cultured at a density of 3000 cells per well in a 384-well plate and allowed to adhere together. 6.25 μLof serum and antibiotic-free DMEM was added to a mixture of plasmid DNA (0.04 μg) and Renilla luciferase phRL-tk (0.01 μg) in the ratio of 4:1, mixed and incubated at room temperature for 5 minutes, thereby obtaining solution A. 1 μL of lipofectin 2000 transfection reagent to 6.25 μLof serum and antibiotic-free DMEM, mixed and incubated at room temperature for 5 minutes, thereby obtaining solution B. The solution A was mixed with the solution B (B was added into A) and incubated at room temperature for 20 minutes, thereby obtaining solution C. The cell culture medium in the 384-well plate was discarded and the cells were washed 2-3 times with PBS. 25 μL of serum containing and antibiotic-free DMEM was added to the 384-well plate followed by incubation. The solution C was added to the 384-well plate, shaken and placed inside a cell culture incubator for 24 hours. The cell culture medium was then discarded and replaced with a certain amount of complete DMEM. Then the cells were treated for 24 hours with a certain concentration of different compounds.

After incubation, the 384-well plate was taken out, allowing the reagents and cells to equilibrate to room temperature of 18-22° C. 60 μL of cell culture medium was aspirated from each well (the remaining culture medium per well was 20 μL), replaced with an equal volume (20 μL) of a detection reagent, and incubated on a shaker in dark at room temperature for 30 minutes. The luciferase activity was analyzed by using a Dual-Luciferase Reporter Assay kit (Promega) and measured by a chemiluminescence analyzer (3010 C chemiluminescence analyzer). All experiments were performed with triplicate cultures.

The fluorescence value of greater than x+3S was used to identify compounds that capable of significantly activating the expression of JWA gene. The compound of the formula I, which is named JAC-4, showed a sharp dose-effect relationship and further described by the following examples.

Example 10

Effect of the small molecule compound JAC-4 on the expression of JWA protein in HBE cells.

The purpose of this embodiment is to verify the accuracy of the screening results through the cell model, and to confirm that JAC-4 does indeed improve the expression of JWA protein.

The HBE cells in the logarithmic growth phase were digested, plated at a density of $5\times10^5$/cell onto a 60 mm cell culture dish, and incubated in different doses of the compound JAC-4 for 24 hours or 48 hours, respectively. The cells were then treated with 0.18 mL of radio immunoprecipitation assay (RIPA, containing 0.5% PMSF) cell lysate for protein extraction, and centrifuged at 12,000×g for 15 minutes. The supernatant was collected and the protein concentration was measured. The proteins were heated and separated by electrophoresis through 12.5% polyacrylamide gel. 70 μg of the heated proteins was loaded into each well and separated by electrophoresis at 60 V for 30 minutes and 90 V for 1-1.5 hours. The proteins were then transferred from the gel to a PVDF membrane using a mini-genie transfer apparatus. The PVDF membrane was blocked with 5% skim milk, incubated at room temperature for 1-2 hours, and washed with TBST (containing 0.1% Tween 20). The washing step was repeated 3 times for 5 minutes each time. The blocked membrane was incubated overnight with primary antibody at 4° C., and then washed with TBS (containing 0.1% Tween 20). The washing step was repeated 3 times for 5 minutes each time. The blocked membrane was incubated at room temperature for 1-2 hours with secondary antibody, and then washed with TBST (containing 0.1% Tween 20). The washing step was repeated 8 times for 5 minutes each time. ECL luminescent liquid was added onto the membrane to enhanced chemiluminescent.

Figures 36, 37:
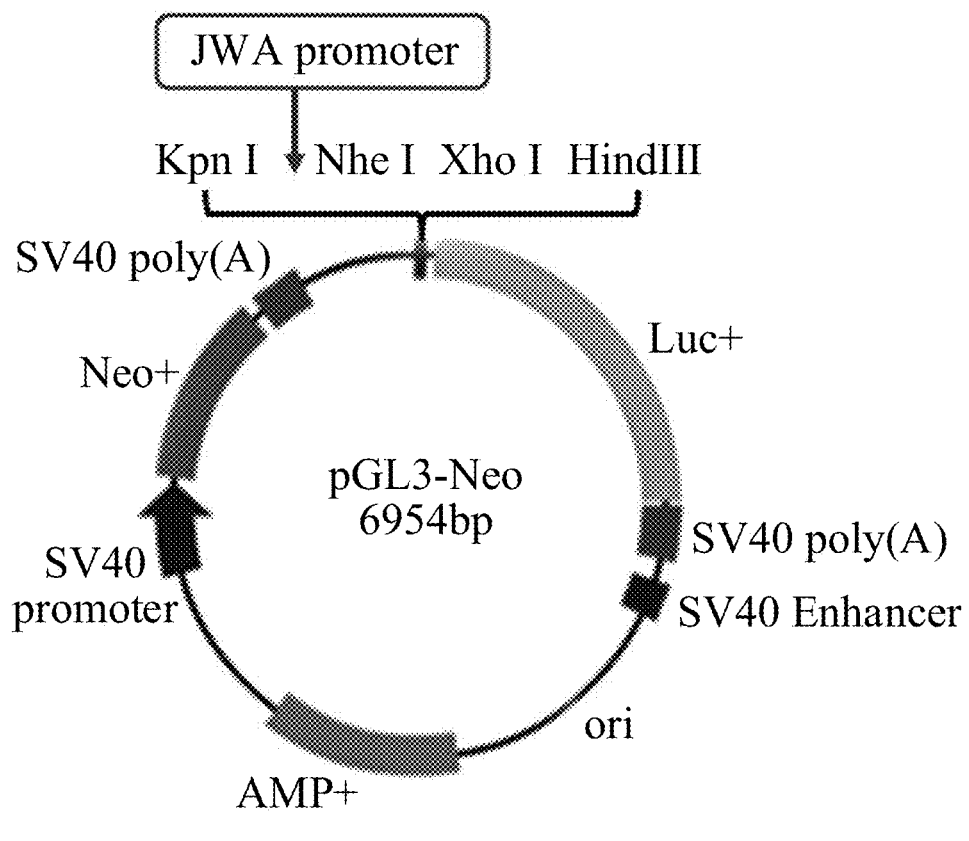
FIG. 36 is a map of a pGL3-JWA-Neo vector comprising JWA promoter in accordance with Example 8 of the disclosure.
FIG. 37 shows a Western blot demonstrating the expression of JWA protein activated by treating HBE cells with compound JAC-4 at different doses in Example 10 of the disclosure; Tubulin is used as an internal reference protein.

Referring to FIG. 37, the expression level of JWA protein was enhanced by treating HBE cells for 24 hours and 48 hours with compound JAC-4 at concentrations of 1, 10, and 100 μmol/L respectively.

Example 11

Preparation of experimental animal feed comprising compound JAC-4.

Figure 38:
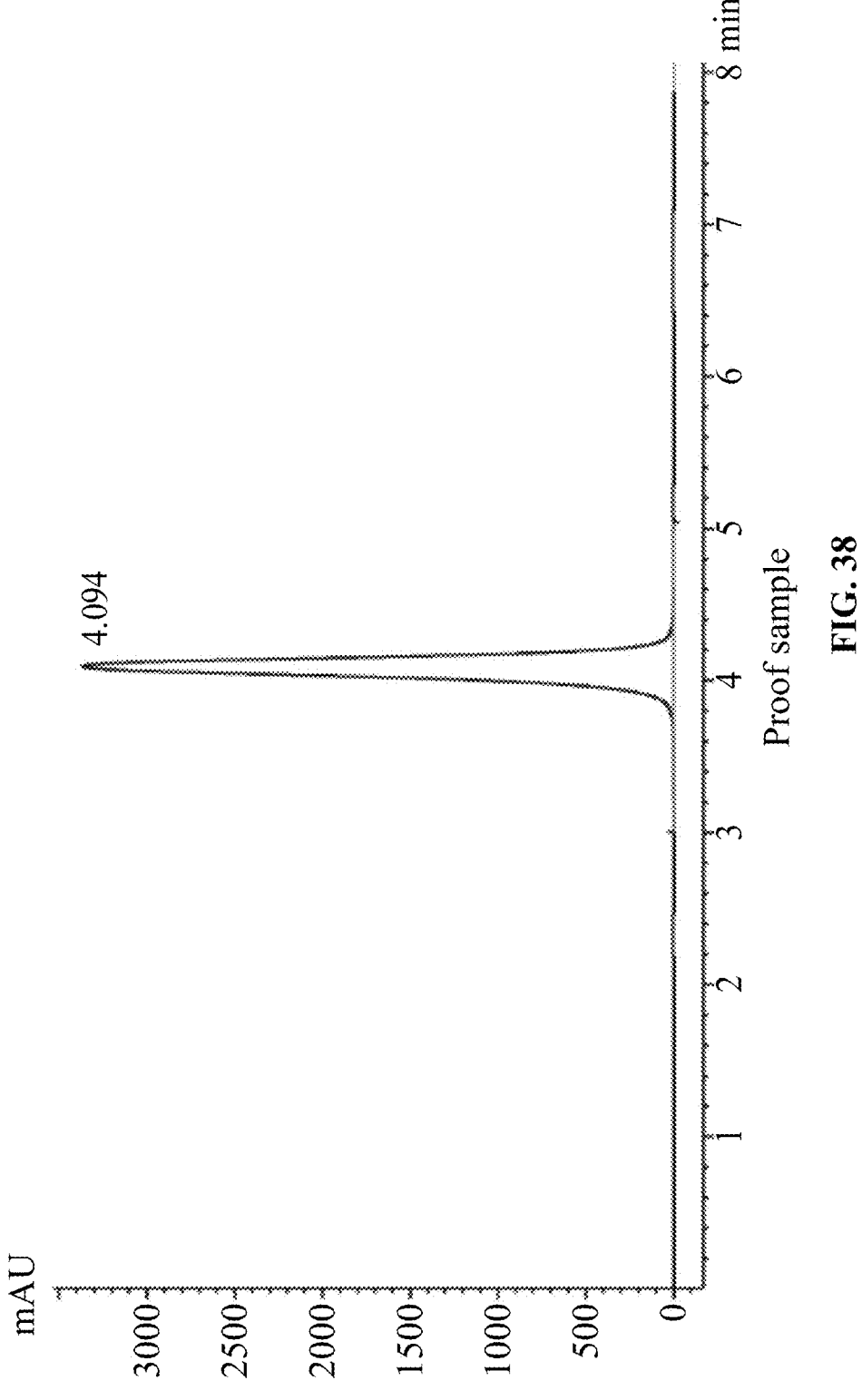
FIGS. 38-40 show the results of high-performance liquid chromatography (HPLC) analysis of compound JAC-4 in test feed in accordance with Example 11 of the disclosure.
Figure 39:
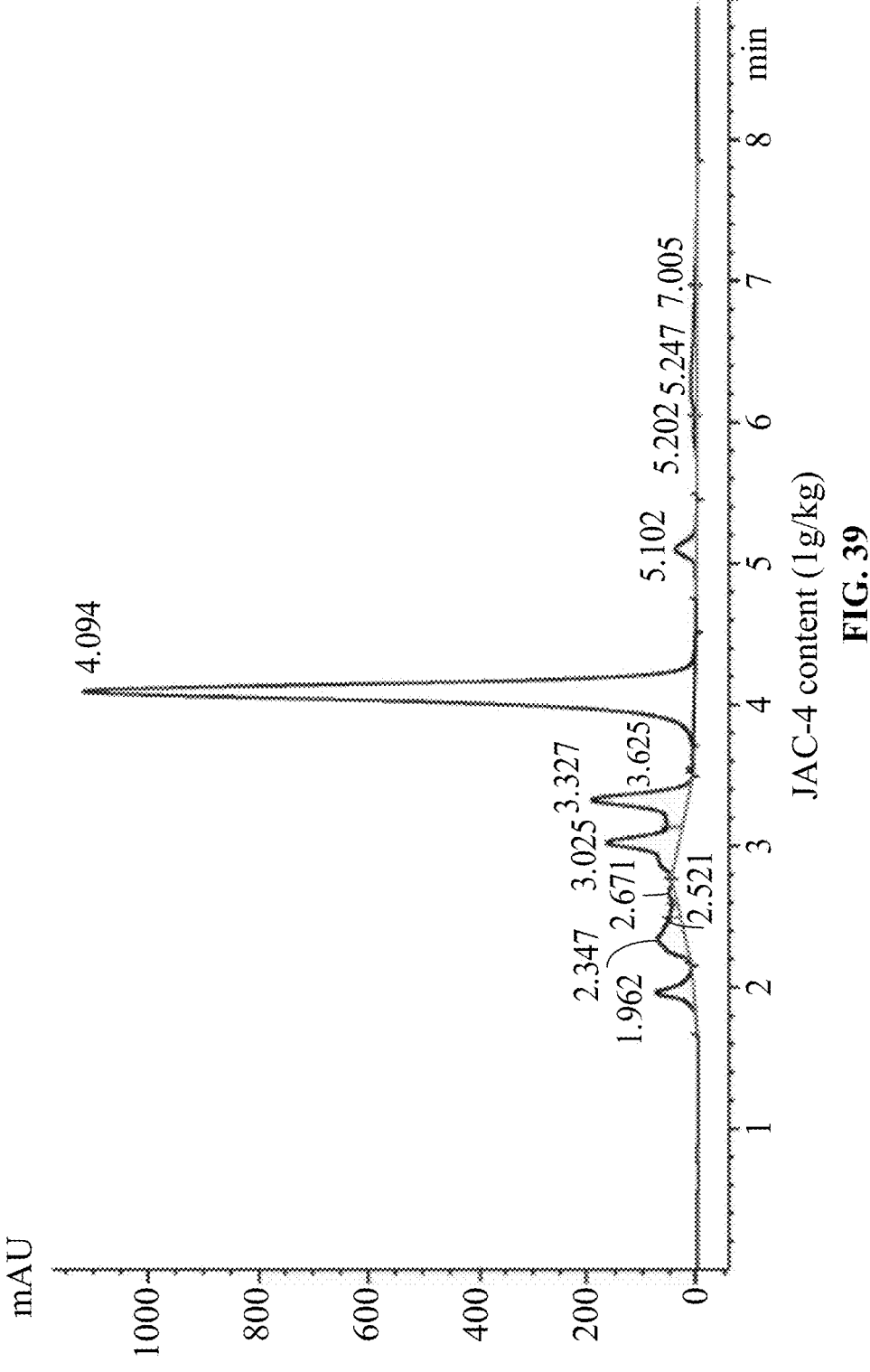
Figure 40:
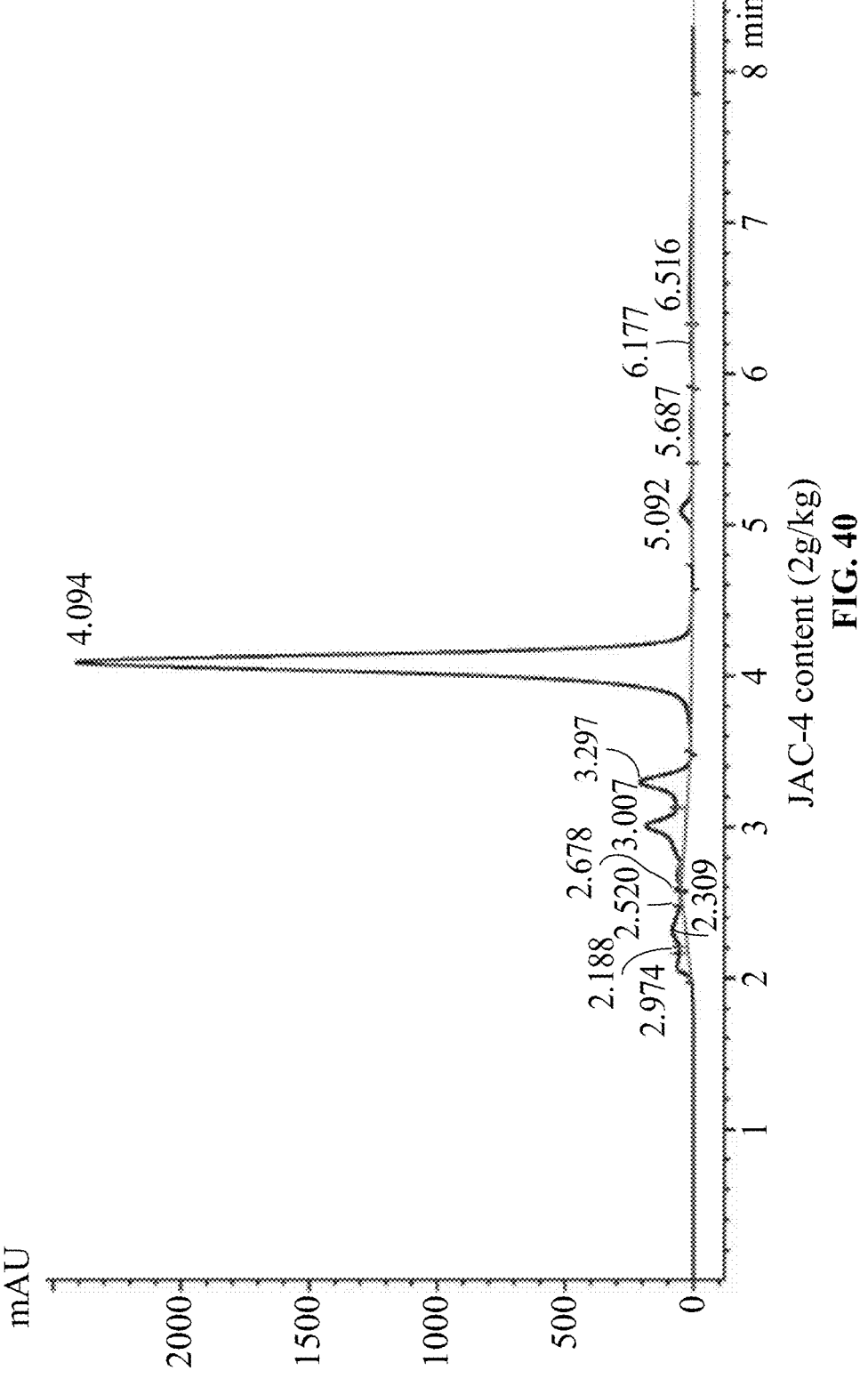

The compound JAC-4 (purity>99%) was mixed with an equal amount of standard mouse feed. Specifically, 1 g of compound JAC-4 was thoroughly mixed with 1 g of basic feed materials; 2 g of the mixture was thoroughly mixed with 2 g of basic feed materials; 4 g of the mixture was thoroughly mixed with 4 g of basic feed materials, and so on, thereby obtaining two test feeds respectively containing 1 g/kg and 2 g/kg of the compound JAC-4. According to the standard operating procedures for feed, the test feeds were processed into pellets, vacuum packaged, and sterilized by a Co60 source irradiation. The feed processing was entrusted to a professional company. To verify that the compound JAC-4 was evenly distributed in the mixed feeds and not damaged in the structure during processing, the sterilized feeds were randomly sampled and fully extracted with organic solvents. The content of the compound JAC-4 was then measured by High Performance Liquid Chromatography and it was confirmed that the compound JAC-4 was not damaged and the content thereof met the requirements (FIGS. 38-40).

Example 12

Feeding 12-month-old mice with the test feed containing 1 g/kg of the compound JAC-4.

12-month-old mice were housed in specific pathogen free (SPF) conditions at an ambient temperature of $22\pm2°$ C. and a relative humidity of 40%-60%, in day/night cycles of 12 h/12 h simulated by lighting. Mice were fed with sterile acidified water, common feeds (without compound JAC-4) or test feeds (with compound JAC-4).

Each mouse had an average body weight of 20 g. In general, the daily feed consumption of each mouse is about 10% of its body weight. Therefore, when the mice consume 1 g/kg of JAC-4 experimental feed, it is equivalent to the daily intake of 100 mg/kg of JAC-4. The mice were weighed every two weeks from the start of feeding and scored on the aging appearance every two weeks from the sixth week. The higher the score, the more obvious the aging appearance. The mice were photographed monthly and changes in appearance were recorded. In all the experiments attention was paid to ethical guidelines for the investigation of experimental pain in conscious animals.

Figure 41:
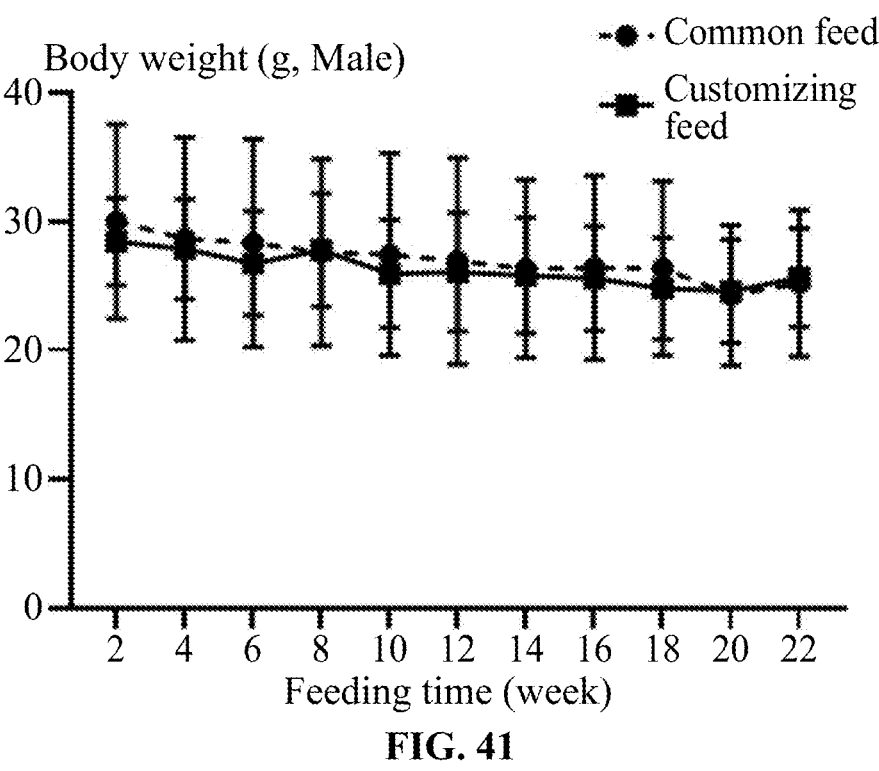
FIGS. 41-42 show body weight curves for the mice (12 months old) fed with test feed (containing 1 g/kg of compound JAC-4) and common feed in accordance with Example 12 of the disclosure.
Figure 42:
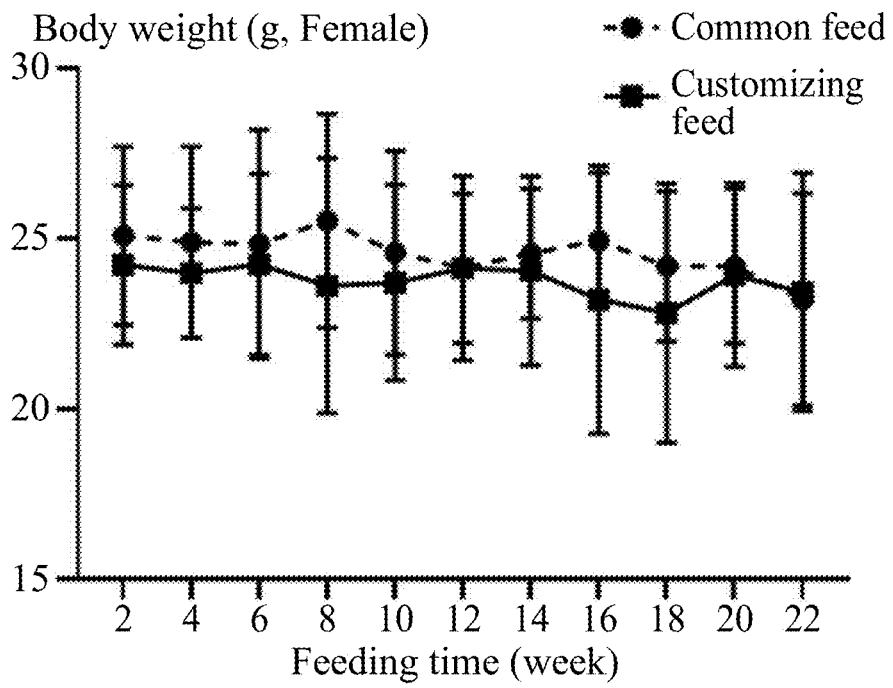
Figure 43:
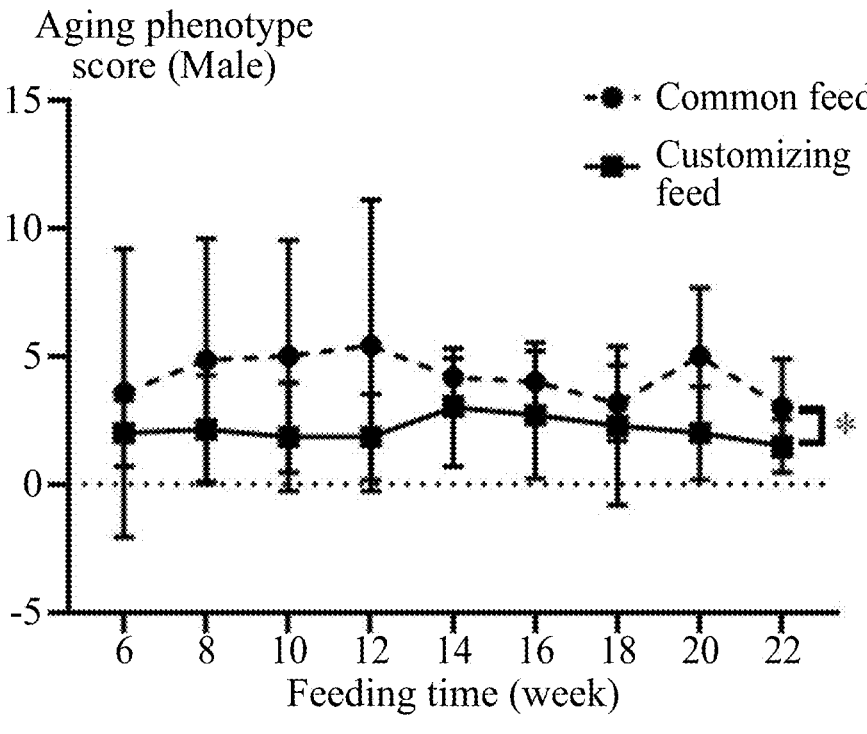
FIGS. 43-44 show scoring curves for the aging phenotype of the mice (12 months old) fed with test feed (containing 1 g/kg of compound JAC-4) and common feed in accordance with Example 12 of the disclosure.
Figure 44:
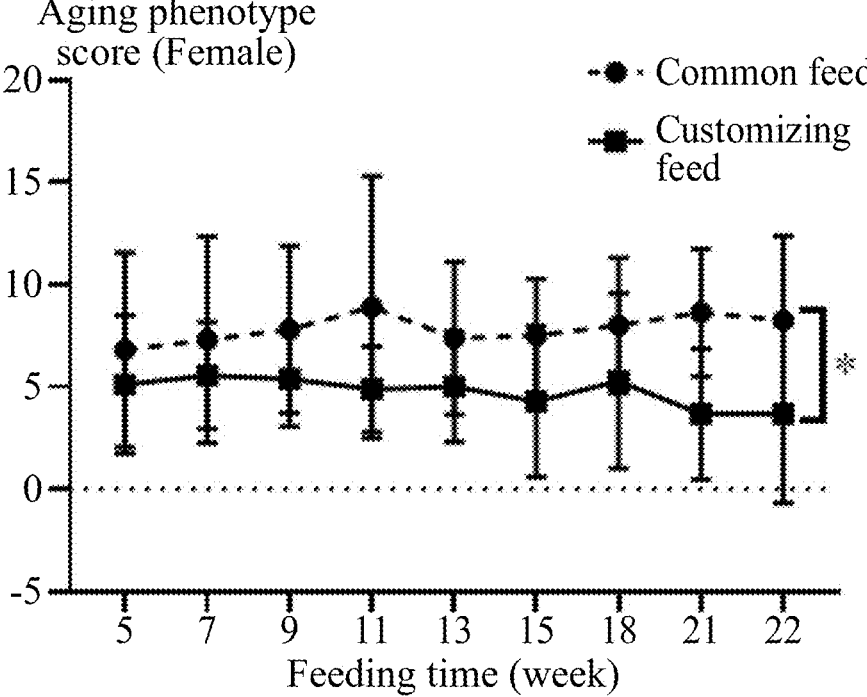
Figure 45:
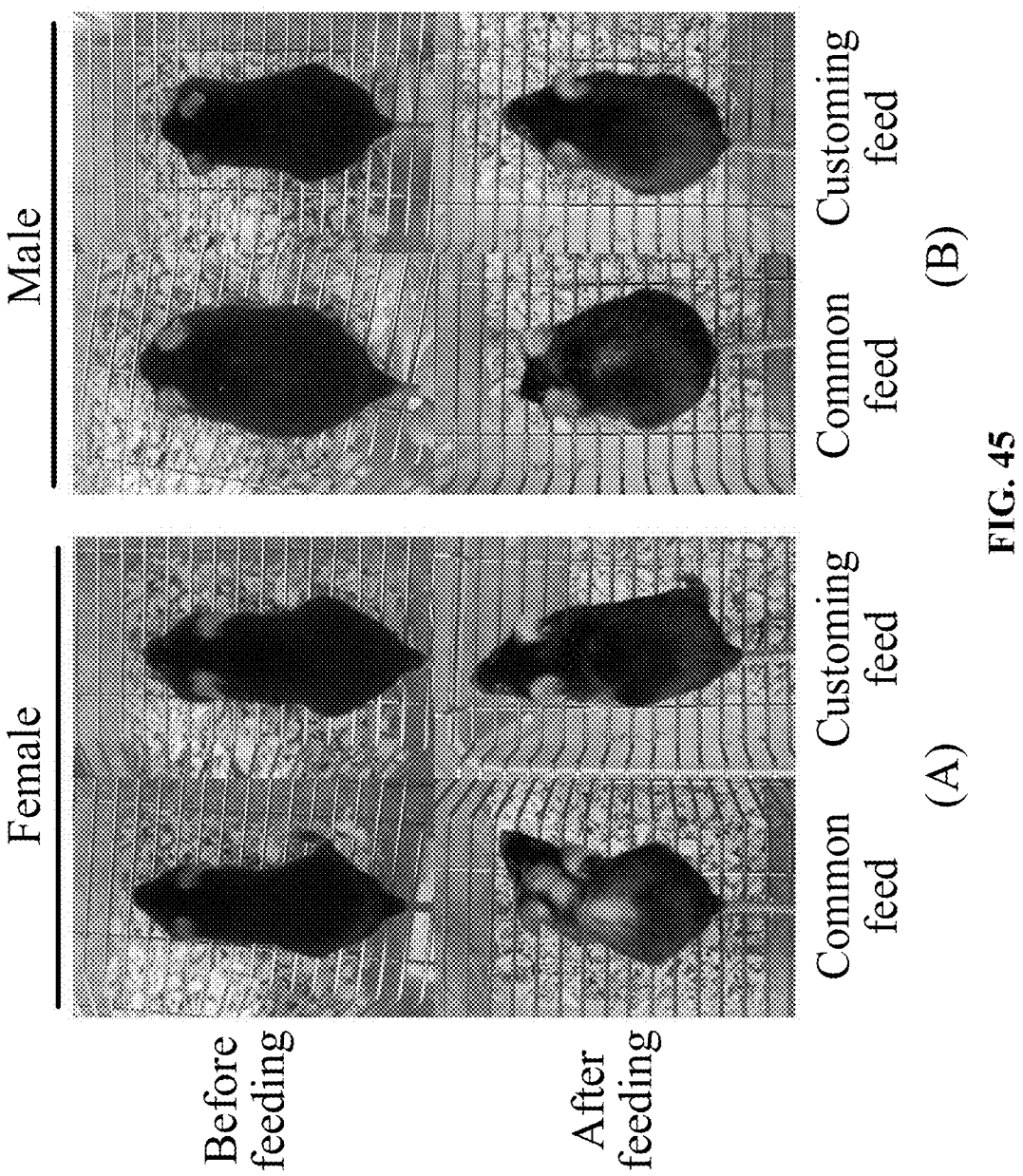
FIG. 45 illustrates a comparison of the appearance of mice (12 months old) before and after being fed with test feed (containing 1 g/kg of compound JAC-4) and common feed in accordance with Example 12 of the disclosure.
Figure 46:
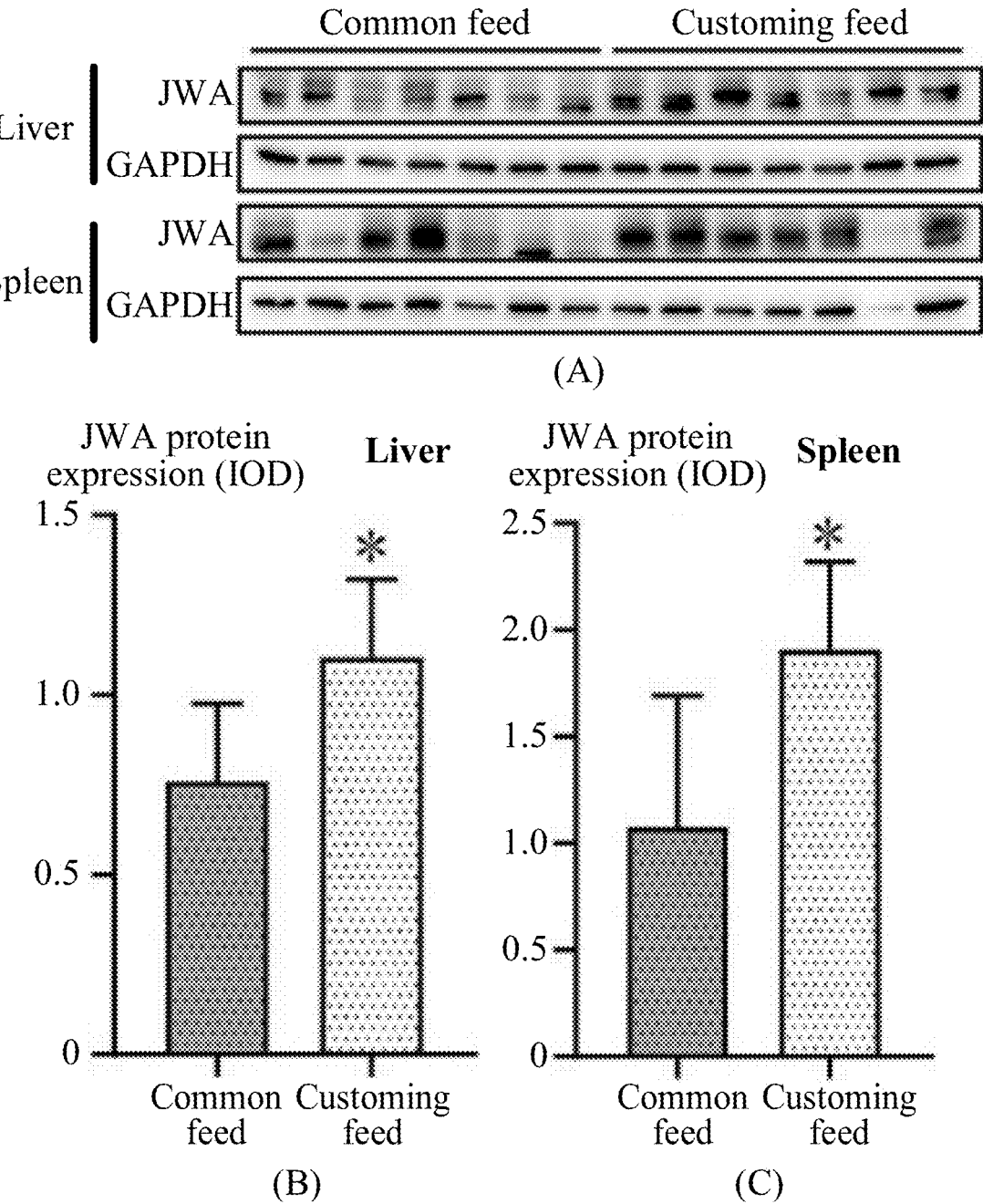
FIG. 46 shows a Western blot demonstrating the expression of JWA protein in liver and spleen tissues of naturally aging mice (24 months old) fed with test feed (containing 2 g/kg of compound JAC-4) in accordance with Example 13 of the disclosure; GAPDH is used as an internal reference protein.
Figure 47:
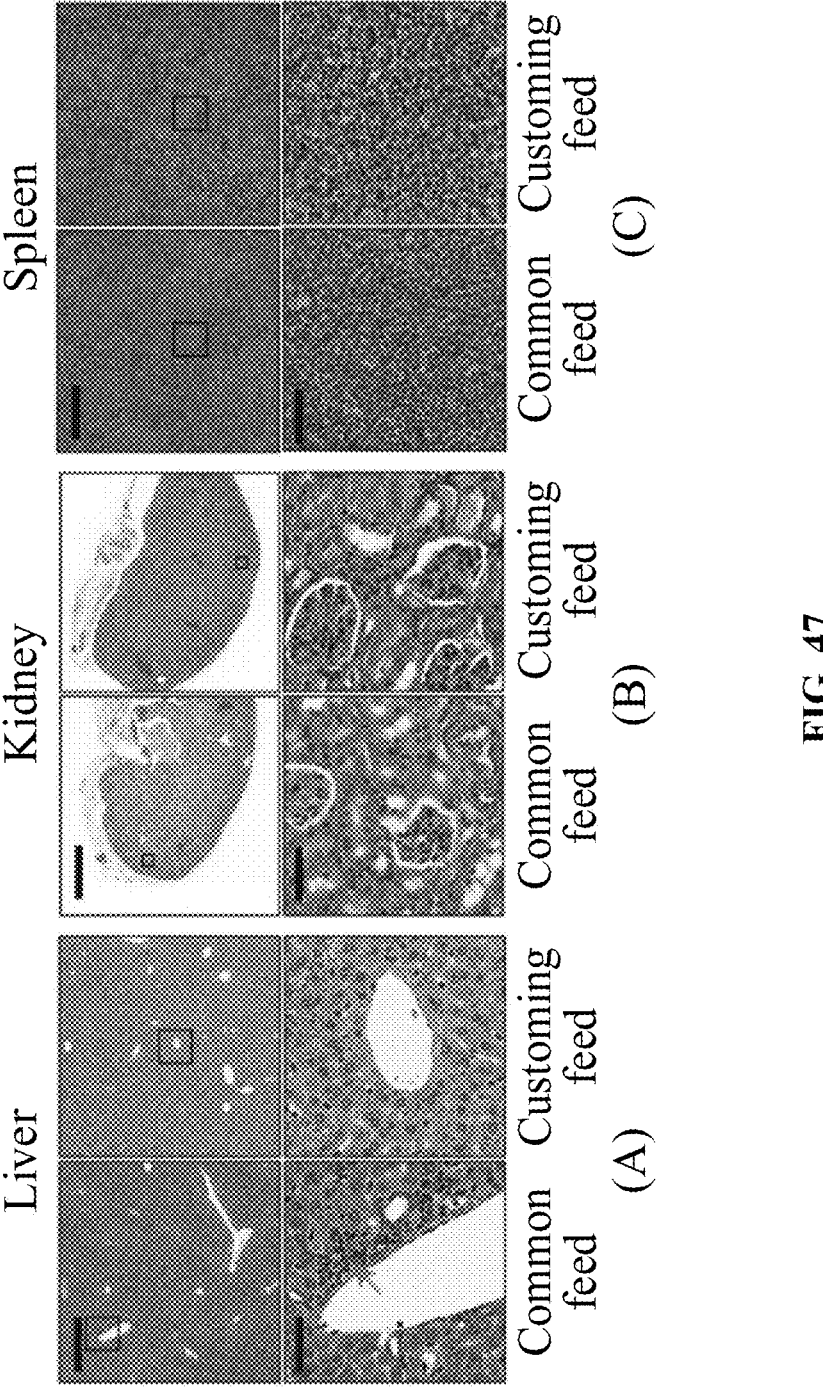
FIG. 47 shows a HE staining demonstrating the liver, spleen and kidney of naturally aging mice (24 months old) fed with test feed (containing 2 g/kg of compound JAC-4)

Referring to FIGS. 41 and 42, at $22^{nd}$ weeks, the mice fed with the test feeds showed a slightly decrease in body weight compared with the mice fed with the common feeds, but no statistical difference. Referring to FIGS. 43 and 44, the mice fed with the test feeds showed a significant decrease in the score of aging appearance compared with the mice fed with the common feeds. Referring to FIG. 45, the mice fed with the test feeds showed a significant decrease in hair loss compared with the mice fed with the common feeds. In conclusion, the results indicate that JAC-4 provides a significant anti-aging effect.

Example 13

Feeding 24-month-old mice with the test feed containing 2 g/kg of the compound JAC-4 (equivalent to 200 mg JAC-4/kg body weight).

Mice were housed in the same conditions as Example 12. After feeding for 10 weeks, the mice were anesthetized. The whole blood was collected, allowed to stand for 30 min at room temperature, and centrifuged at 3000 rpm for 15 min. The supernatant, i.e., serum, was collected and analyzed by Hitachi 7100 automatic biochemical analyzer. Liver, spleen and kidney tissues of the mice were isolated on ice, fixed with 4% paraformaldehyde, or frozen at $-80°$ C. The fixed tissues were processed into a paraffin section or frozen section with a thickness of 5 $\mu$m, stained with HE to visualize the morphological and pathological changes in the liver, spleen and kidney. The liver section was stained with oil red O for fat deposition and stained with periodic acid-Schiff (PAS) for glycogen. Total protein was extracted from the liver and spleen frozen at $-80°$ C., and cell membrane proteins were extracted from the liver frozen at $-80°$ C. Western blot was performed to detect the expression of JWA protein in liver and spleen tissues, the expression of p-AKT, AKT, p-GSK3$\beta$ and GSK3$\beta$ proteins in liver tissues, and the expression of glucose transporter (Glut 2) in cell membrane proteins of liver tissues. A biochemical kit (purchased from Nanjing Jiancheng Bioengineering Institute, Nanjing, China) was used to detect the activities of Superoxide dismutase (SOD), as well as the main rate-limiting enzymes of glucose and lipid metabolism in liver tissues. In all the experiments attention was paid to ethical guidelines for the investigation of experimental pain in conscious animals.

Referring to FIGS. 46-52, after feeding the test feed containing compound JAC-4, the expression of JWA protein in the liver and spleen tissues of aging mice increased significantly. The compound JAC-4 did not produce observable abnormal changes in the morphology of mouse liver, kidney and spleen, and significantly reduced age-related inflammatory cell infiltration around the central vein of the liver. JAC-4 feeds also significantly reduced the serum glucose and triglycerides stored in naturally aging mice and increased the glycogen synthesis in the liver. Experimental results further indicated that the compound JAC-4 increased the rate-limiting enzyme related to glucose decomposition and the glycogen synthase in the liver, increased Glut 2 expression, activated AKT phosphorylation, and inhibited GSK3$\beta$ to promote glycogen synthesis.

In conclusion, the compound JAC-4 activated JWA gene expression and thus delayed aging and maintained homeostasis in mice.

It will be obvious to those skilled in the art that changes and modifications may be made, and therefore, the aim in the appended claims is to cover all such changes and modifications.

What is claimed is:

1. A method for treatment of atherosclerosis and type 2 diabetes in an animal that is free of tumors, the method comprising administering a pharmaceutically effective amount of a compound of formula (I) or a pharmaceutically acceptable salt thereof to the animal that is free of tumors:

I

2. The method of claim 1, wherein the pharmaceutically acceptable salt is prepared by mixing the compound with hydrochloric acid, sulfuric acid, benzenesulfonic acid, p-toluenesulfonic acid, phosphoric acid, hydrobromic acid, maleic acid, fumaric acid, or malic acid.

3. The method of claim 1, wherein the compound of formula (I) or the pharmaceutically acceptable salt thereof is in the form of a food additive, healthcare product, medicine, or pharmaceutical composition.

4. The method of claim 3, wherein the compound of formula (I) or the pharmaceutically acceptable salt thereof is a food additive;

the method comprises administering a food comprising the food additive to the animal; and a ratio of a weight of the compound of formula (I) or the pharmaceutically acceptable salt thereof in the food to a weight of the food is 1-2 g/kg.

\*    \*    \*    \*    \*